(12) United States Patent
Hunt et al.

(10) Patent No.: US 10,035,810 B2
(45) Date of Patent: Jul. 31, 2018

(54) 5,6-DIHYDRO-4H-BENZO[B]THIENO-[2,3-D] AZEPINE DERIVATIVE

(71) Applicant: PULMOCIDE LIMITED, London (GB)

(72) Inventors: Simon Fraser Hunt, Nottingham (GB); Stuart Thomas Onions, Nottingham (GB); Vladimir Sherbukhin, Nottingham (GB); Euan Alexander Fraser Fordyce, Nottingham (GB); Peter John Murray, London (GB); Daniel William Brookes, London (GB); Kazuhiro Ito, London (GB); Peter Strong, London (GB)

(73) Assignee: PULMOCIDE LIMITED, London (GB)

( * ) Notice: Subject to any disclaimer, the term of this patent is extended or adjusted under 35 U.S.C. 154(b) by 0 days.

(21) Appl. No.: 15/902,077

(22) Filed: Feb. 22, 2018

(65) Prior Publication Data

US 2018/0179228 A1    Jun. 28, 2018

Related U.S. Application Data

(63) Continuation of application No. 15/642,637, filed on Jul. 6, 2017, now Pat. No. 9,926,335, which is a continuation of application No. 15/305,003, filed as application No. PCT/GB2015/052944 on Oct. 8, 2015, now Pat. No. 9,732,098.

(30) Foreign Application Priority Data

Oct. 10, 2014  (EP) ..................... 14188494

(51) Int. Cl.
| | |
|---|---|
| *C07D 519/00* | (2006.01) |
| *C07D 495/04* | (2006.01) |
| *A61K 31/55* | (2006.01) |
| *A61K 45/06* | (2006.01) |
| *A61K 9/14* | (2006.01) |
| *A61K 9/10* | (2006.01) |

(52) U.S. Cl.
CPC .............. *C07D 519/00* (2013.01); *A61K 9/10* (2013.01); *A61K 9/14* (2013.01); *A61K 31/55* (2013.01); *A61K 45/06* (2013.01)

(58) Field of Classification Search
None
See application file for complete search history.

(56) References Cited

U.S. PATENT DOCUMENTS 8,999,969 B2  4/2015 Mackman et al.

FOREIGN PATENT DOCUMENTS

| WO | 97/47625 | 12/1997 |
|---|---|---|
| WO | 00/64876 | 11/2000 |
| WO | 2011/005842 A1 | 1/2011 |
| WO | 2011/046954 A1 | 4/2011 |
| WO | 2012/016217 A1 | 2/2012 |
| WO | 2012/129562 A2 | 9/2012 |
| WO | 2016/022464 A1 | 2/2016 |
| WO | 2017123884 | 7/2017 |

OTHER PUBLICATIONS

Coates, M. et al; Antimicrob. Agents and Chem., (2017) 61 (9), 1-18—"Preclinical Characterization of PC786, an Inhaled Small-Molecule Respiratory Syncytial Virus L Protein Polymerase Inhibitor".

Yajun Zheng et al.—Bioorganic & Medicinal Chemistry Letters 24 (2014) 3673-3682—"The use of spirocyclic scaffolds in drug discovery".

Sudo, et al.—Antiviral Research (2005) vol. 65: 125-131—"YM-53403, a unique anti-respiratory syncytial virus agent with a novel mechanism of action".

Kiong, et al—Bioorganic & Medicinal Chemistry Letters (2013) vol. 23 No. 24: 6789-6793—"Discovery of a potent respiratory syncytial virus RNA polymerase inhibitor".

*Primary Examiner* — Michael Barker
(74) *Attorney, Agent, or Firm* — Klauber & Jackson LLC

(57) ABSTRACT

There is provided a 5,6-dihydro-4H-benzo[b]thieno-[2,3-d] azepine derivative which is useful in the treatment of respiratory syncytial virus (RSV) infection and for the prevention of disease associated with RSV infection. (Formula (1)).

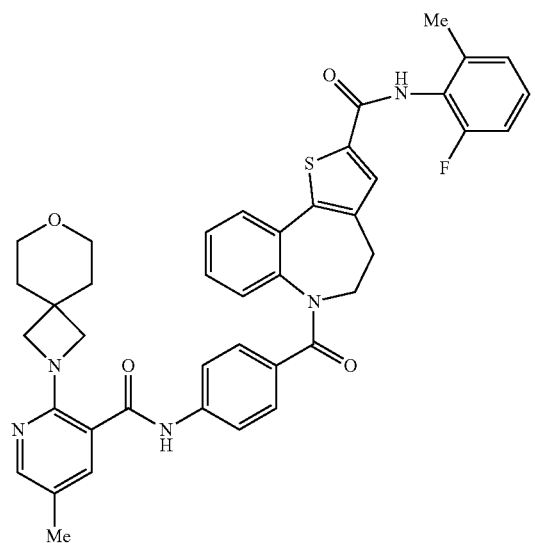

7 Claims, 2 Drawing Sheets

5,6-DIHYDRO-4H-BENZO[B]THIENO-[2,3-D] AZEPINE DERIVATIVE

CROSS REFERENCE TO RELATED APPLICATIONS

The present application is a Continuation of co-pending U.S. Non-provisional application Ser. No. 15/646,637 filed Jul. 6, 2017, which in turn, is a Continuation of U.S. Non-provisional application Ser. No. 15/305,003 filed Oct. 18, 2016, now U.S. Pat. No. 9,732,098 issued Aug. 15, 2017, which in turn, is a National Stage Application claiming priority from PCT Application No. PCT/GB2015/052944, filed Oct. 8, 2015, which in turn, claims priority from European Application No. 14188494.0, filed Oct. 10, 2014. Applicants claim the benefits of 35 U.S.C. § 120 as to the Non-provisional U.S. applications and the PCT application, and priority under 35 U.S.C. § 119 as to the said European application, and the entire disclosures of all applications are incorporated herein by reference in their entireties.

FIELD OF THE INVENTION

The invention relates to a novel compound, compositions containing the same, processes for making said compound and its use in therapy. The compound of the invention is intended to treat or prevent respiratory syncytial virus infections and associated disease particularly infections caused by the A and B strains thereof.

BACKGROUND OF THE INVENTION

Human respiratory syncytial virus (RSV) is a pneumovirus of the paramyxovirus family and the most common cause of bronchiolitis and pneumonia in infants under one year of age. Most children become infected with RSV prior to their second birthday resulting in 75-125,000 hospitalisations. The associated medical costs are thought to exceed $650 million annually in the United States alone. In addition, early-life respiratory viral infections, notably with RSV, increase the risk of the subsequent development of childhood asthma (Holt and Sly, 2002.). RSV infection can produce severe, lower respiratory tract disease in patients of any age. The elderly, as well as those having compromised cardiac, pulmonary or immune systems are particularly vulnerable and it is estimated that some 14,000 deaths occur annually in the United States in subjects over 65 years old. In addition, RSV infection is increasingly regarded as an important precipitator of exacerbations in patients suffering from chronic obstructive pulmonary disease (COPD) (Mohan et al., 2010) as well as asthma (Newcomb and Peebles, 2009) and cystic fibrosis (Abman et al., 1988). In immunocompromised adults, approximately 50% of upper respiratory tract infections with RSV progress to pneumonia.

The initial portal of entry by RSV is through the nose or eye rather than the mouth (Hall et al., 1981). Once established in the upper respiratory tract the virus is able to migrate readily into the lungs. The pathophysiology of RSV infection was investigated in a study of lung tissues obtained from deceased children (Johnson et al., 2007). Examination of tissues from four individuals revealed immunostaining of epithelial cells indicating the presence of RSV, without basal cells being affected. The epithelial localisation of the pathogenic organism provides a challenge to treatment since a supra-effective concentration of the drug substance has to be maintained at the discrete cellular site to enable the infection to be treated and subsequently cleared.

The RSV virus exists as two antigenic sub-groups: A and B. Viruses of the RSV A strain were formerly regarded as the sub-group pathogens responsible for the majority of clinical disease and were reported to produce a more symptomatic pathology (Walsh et al., 1997; Panayiotou et al., 2014). A common RSV A strain is RSV A2 (Olivier et al., 2009). However, during a recent outbreak in China virus strains from the RSV B sub-group were found to predominate in the afflicted population (Zhang et al., 2010).

Over the last two decades considerable progress has been made in the treatment of a number of viral diseases including human immunodeficiency virus (HIV) and both hepatitis B and hepatitis C. In all these cases gold standard therapies have evolved that consist of combination treatments that were brought about, at least to some extent, in response to the emergence of drug resistant disease.

FDA-approved drugs for the treatment of acute RSV infections comprise of (aerosolised) ribavirin and the humanized, monoclonal antibody, palivizumab (Synagis). The latter agent targets the RSV fusion (F) protein and is limited to prophylactic use in high risk paediatric patients. Furthermore, clinical variants resistant to neutralisation by palivizumab were recently identified (Zhu et al., 2011) and therefore no truly effective vaccine is currently available. The use of ribavirin is limited by its low potency against the virus and by concerns over its side-effect profile. Consequently there is an urgent, unmet need for the discovery of novel, safe and effective therapies against RSV infection having an improved clinical profile. Moreover, in view of the emerging prominence of the RSV B strains in clinical disease it is highly desirable that these treatments be efficacious against infections arising from both RSV A and RSV B strains.

SUMMARY OF THE INVENTION

In a first aspect, the invention provides a compound of formula (I),

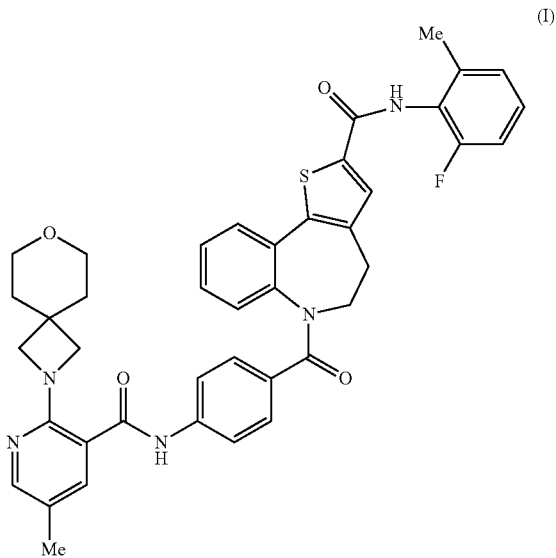 [SMILES: Cc1cnc(N2CC3(CCOCC3)C2)c(C(=O)Nc2ccc(C(=O)N3CCc4cc(C(=O)Nc5c(C)cccc5F)sc4-c4ccccc43)cc2)c1]

which is: N-(2-fluoro-6-methylphenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide.

or a pharmaceutically acceptable salt thereof ("the compound of the invention").

Biological data disclosed herein reveals that the compound of the invention inhibits the cytopathic effect associated with infection by RSV A strains, and also inhibits the cytopathic effect associated with infection by RSV B strains.

DETAILED DESCRIPTION OF THE INVENTION

Figure 1:
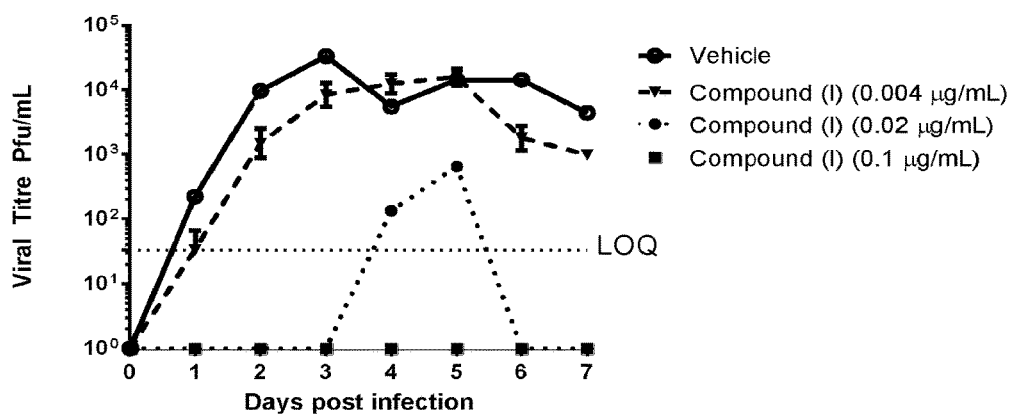
FIG. 1 shows the effect of Compound (I) on virus titre in RSV A2 infected air-liquid interface (ALI) cultured epithelial cells following early intervention with test compound

Pharmaceutically acceptable salts of the compound of formula (I) include in particular pharmaceutically acceptable acid addition salts of the said compound. The pharmaceutically acceptable acid addition salts of the compound of formula (I) are meant to comprise the therapeutically active non-toxic acid addition salts that the compound of formula (I) is able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Salts as referred to herein, for example in relation to intermediate compounds, include pharmaceutically acceptable salts, such as those above mentioned, as well as other salts that may be disfavoured for pharmaceutical use. Salts of acidic compounds include salts formed with positive ions of Group 1 and Group 2 metals including, sodium, potassium, calcium and magnesium ions as well as with inorganic cations such as ammonium ion.

The definition of the compound of formula (I) is intended to include all stereoisomers of said compound. Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

The definition of the compound of formula (I) is intended to include all tautomers of said compound.

The definition of the compound of formula (I) is intended to include all solvates of said compound (including solvates of salts of said compound) unless the context specifically indicates otherwise. Examples of solvates include hydrates.

The compound of the disclosure includes isotopic variants in which one or more specified atom(s) is/are naturally occurring or non-naturally occurring isotopes. In one embodiment the isotope is a stable isotope. Thus the compound of the disclosure includes, for example deuterium labelled versions and the like.

The disclosure also extends to all polymorphic forms of the compound herein defined.

Novel intermediates as described herein [such as, for example, compounds of formula (II), (III), (IV), (VI) and (X)] form a further aspect of the invention, as do salts thereof (such as pharmaceutically acceptable salts).

The compound of the invention is useful as a pharmaceutical.

In an embodiment there is provided a pharmaceutical composition comprising the compound of the invention optionally in combination with one or more pharmaceutically acceptable diluents or carriers.

Suitably the compound of the invention is administered topically to the lung or nose, particularly, topically to the lung. Thus, in an embodiment there is provided a pharmaceutical composition comprising the compound of the invention optionally in combination with one or more topically acceptable diluents or carriers.

Suitably compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising the compound of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 μm or a $D_{50}$ of 0.5-10 μm e.g. around 1-5 μm. Powders of the compound of the invention in finely divided form may be prepared by a micronisation process or similar size reduction process. Micronisation may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronisation, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TVVISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

The compound of the invention is useful in the treatment of RSV infection and for the prevention or treatment of disease associated with RSV infection.

In an aspect of the invention there is provided use of the compound of the invention for the manufacture of a medicament for the treatment of RSV infection and for the prevention or treatment of disease associated with RSV infection.

In another aspect of the invention there is provided a method of treatment of a subject infected with RSV which comprises administering to said subject an effective amount of the compound of the invention.

In another aspect of the invention there is provided a method of prevention or treatment of disease associated with RSV infection in a subject which comprises administering to said subject an effective amount of the compound of the invention.

The compound of the invention may be used in a prophylactic setting by its administration prior to infection.

In one embodiment the RSV infection is RSV A strain infection (e.g. with an RSV A2 strain). In another embodiment the RSV infection is RSV B strain infection (e.g. with RSV B Washington strain).

Subjects include human and animal subjects, especially human subjects.

The compound of the invention is especially useful for the treatment of RSV infection and for the prevention or treatment of disease associated with RSV infection in at risk subjects. At risk subjects include premature infants, children with congenital defects of the lung or heart, immunocompromised subjects (e.g. those suffering from HIV infection), elderly subjects and subjects suffering from a chronic health condition affecting the heart or lung (e.g. congestive heart failure or chronic obstructive pulmonary disease).

The compound of the invention may be administered in combination with a second or further active ingredient. The compound of the invention may be co-formulated with a second or further active ingredient or the second or further active ingredient may be formulated to be administered separately by the same or a different route. According to an aspect of the invention there is provided a kit of parts comprising (a) a pharmaceutical composition comprising the compound of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to RSV infection.

Second or further active ingredients include active ingredients suitable for the treatment or prevention of RSV infection or disease associated with RSV infection or conditions co-morbid with RSV infection.

Second or further active ingredients may, for example, be selected from anti-viral agents (such as other anti-RSV agents) including F protein inhibitors (including anti-F-protein antibodies, such as palivizumab), RNA polymerase inhibitors and ribavirin and anti-inflammatory agents.

The compound of the invention may be administered at a suitable interval, for example once per day, twice per day, three times per day or four times per day.

A suitable dose amount for a human of average weight (50-70 kg) is expected to be around 50 µg to 10 mg/day e.g. 500 µg to 5 mg/day although the precise dose to be administered may be determined by a skilled person.

The compound of the invention is expected to have one or more of the following favourable attributes:
potent inhibition of cytopathic effect and/or virus replication and/or F-protein expression in humans (or an animal model, or an in vitro system) caused by RSV A strains, such as the A2 strain;
potent inhibition of cytopathic effect and/or virus replication and/or F-protein expression in humans (or an animal model, or an in vitro system) caused by RSV B strains;
long duration of action in lungs, preferably consistent with once daily dosing; and
acceptable safety profile, especially following topical administration to the lung or nose.

Experimental Section

Abbreviations used herein are defined below (Table 1). Any abbreviations not defined are intended to convey their generally accepted meaning.

TABLE 1

| Abbreviations | |
| --- | --- |
| ALI | air liquid interface |
| aq | aqueous |
| BALF | bronchoalveolar lavage fluid |
| BEAS2B | SV40-immortalised human bronchial epithelial cell line |
| br | broad |
| BSA | bovine serum albumin |
| $CC_{50}$ | 50% cell cytotoxicity concentration |
| conc | concentrated |
| CPE | cytopathic effect |
| d | doublet |
| DAB | 3,3'-diaminobenzidine |
| DCM | dichloromethane |
| DMEM | Dulbecco's Modified Eagle Medium |
| DMF | N,N-dimethylformamide |
| DMSO | dimethyl sulfoxide |
| DSS | dextran sodium sulphate |
| (ES+) | electrospray ionization, positive mode |
| Et | ethyl |
| EtOAc | ethyl acetate |
| FBS | foetal bovine serum |
| Hep2 | human laryngeal epithelioma cell line 2 |
| HPLC | reverse phase high performance liquid chromatography |
| hr | hour(s) |
| HRP | horse radish peroxidase |
| $IC_{50}$ | 50% inhibitory concentration |
| $IC_{75}$ | 75% inhibitory concentration |
| $IC_{90}$ | 90% inhibitory concentration |
| IgG | immunogloblin G |
| m | multiplet |
| $(M + H)^+$ | protonated molecular ion |
| Me | methyl |
| MHz | megahertz |
| MMD | mass median diameter |
| MOI | multiplicity of infection |
| min | minute(s) |
| m/z | mass-to-charge ratio |
| NMP | N-methylpyrrolidine |
| NMR | nuclear magnetic resonance (spectroscopy) |
| nt | not tested |
| OD | optical density |
| PBS | phosphate buffered saline |
| PCR | polymerase chain reaction |

TABLE 1-continued

| Abbreviations | |
| --- | --- |
| Pen Srep | Penicillin-Streptomycin |
| PFU | plaque forming unit |
| prep HPLC | preparative high performance liquid chromatography |
| q | quartet |
| RT | room temperature |
| RPMI | Roswell Park Memorial Institute medium |
| RSV | respiratory syncytial virus |
| s | singlet |
| sat | saturated |
| SDS | sodium dodecyl sulphate |
| t | triplet |
| THF | tetrahydrofuran |
| TLC | thin layer chromatography |
| TMB | 3,3',5,5'-tetramethylbenzidine |
| vol | volume(s) |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography:

Waters X-Select CSH column C18, 5 µm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Analytical and Spectroscopic Methods

Reverse Phase HPLC Conditions for LCMS Analysis:

Waters Xselect CSH C18 XP column, 2.5 µm (4.6×30 mm) at 40° C.; flow rate 2.5-4.5 mL min$^{-1}$ eluted with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01 3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

$^1$H NMR Spectroscopy:

Spectra were acquired on a Bruker Avance III spectrometer at 400 MHz using residual undeuterated solvent as reference and unless specified otherwise were run in DMSO-$d_6$.

Methods for the Synthesis of Compound (I)

Non limiting synthetic strategies which have been used to prepare the compound of the present invention are summarised below (Scheme 1). All of the disclosed routes to Compound (I) originate from the azepine derivative, intermediate (VIIIa), which is readily accessible, in three steps, from commercially available starting materials. The principal variations arise from the order in which the synthetic transformations are applied to the said key intermediate (VIIIa) thereby generating three different precursors to compound (I): namely Intermediates (II), (III) and (IV). Route 1, comprises of the amide coupling of the thiophene carboxylic acid (II) with 2-fluoro-6-methylaniline. An alternative preparative method, Route 2, exploits the formation of compound (I) from the 2-chloronicotinamide intermediate (III) by an S$_N$Ar displacement reaction with the spirocyclic amine: 7-oxa-2-azaspiro[3.5]nonane. This procedure has been scaled up to provide compound (I) in a single batch of over 0.5 kg and this synthetic campaign is also described herein below. A third approach to compound (I) is Route 3, which consists of an amide coupling reaction between the aniline (IV) and the pre-formed 2-aminonicotinic acid (VI).

Scheme 1: Synthetic routes used for the preparation of Compound (I).

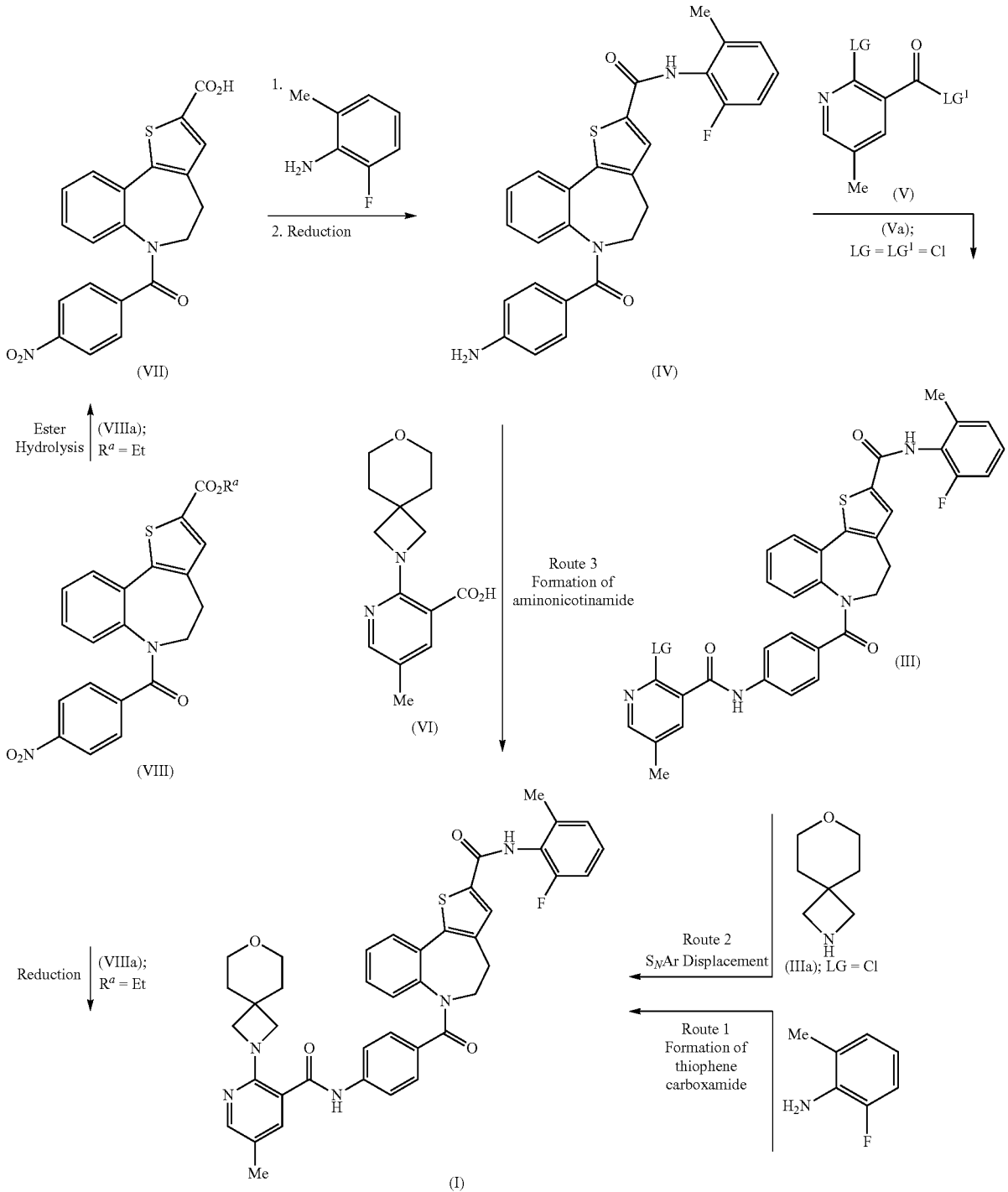

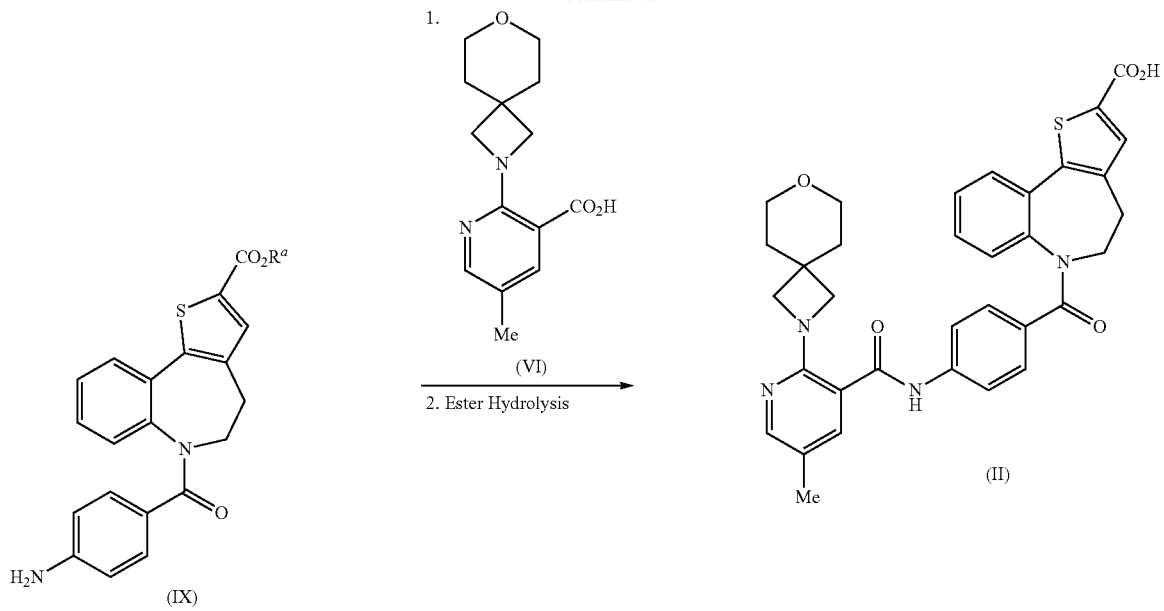

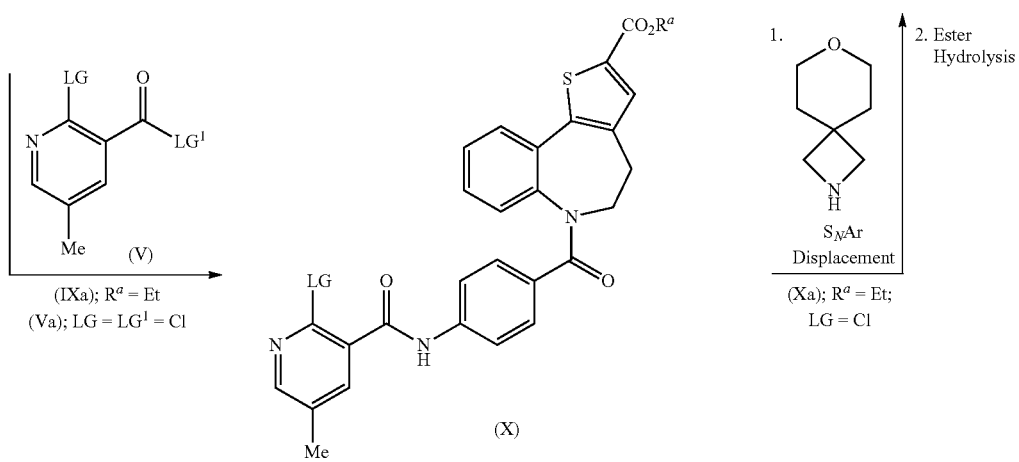

The generic groups LG and LG¹ in Scheme 1 represent leaving groups, such that the resulting compounds are converted into reactive electrophiles. Examples of suitable leaving groups include halogen atoms such as Cl and Br, in which Cl is typically preferred due to the ready availability and use of reagents for their formation. Those skilled in the art will appreciate that further examples of common leaving groups, used in this context, include mesylate, tosylate or triflate [p-trifluomethylsulfonate]). A review of methodologies for the preparation of amides is covered in: '*Amide bond formation and peptide coupling*' Montalbetti, C. A. G. N. and Falque, V. *Tetrahedron*, 2005, 61, 10827-10852. In the present case the alkyl group $R^a$ is ethyl and, more generally, is lower alkyl such as $C_{1-6}$alkyl or $C_{1-4}$alkyl.

Ethyl 2-chloro-5-methylnicotinate

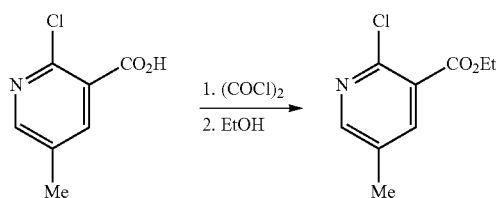 [SMILES: Cc1cnc(Cl)c(C(=O)O)c1 ; CCOC(=O)c1cc(C)cnc1Cl]

To a solution of 2-chloro-5-methylnicotinic acid (3.90 g, 22.7 mmol) in DCM (100 mL) was added oxalyl chloride (9.95 mL, 114 mmol) followed by 1 drop of DMF. The resulting mixture was stirred at RT for 30 min and evaporated in vacuo. The residue thus obtained was taken up into EtOH (66 mL), stirred for a further 2 hr and then evaporated in vacuo. The crude product obtained was purified by flash column chromatography (SiO$_2$, 120 g, 0-50% DCM in isohexane, gradient elution) to afford the title compound as a colourless oil (3.71 g, 82% yield); $^1$H NMR δ: 1.32 (3H, t), 2.34 (3H, s), 4.34 (2H, q), 8.06-8.07 (1H, m), 8.41-8.43 (1H, m). [See also: Yamamoto S. et al., *Bioorg. Med. Chem.* 2012, 20, 422-434.]

Ethyl 5-methyl-2-(7-oxa-2-azaspiro[3.5]nonan-2-yl) nicotinate

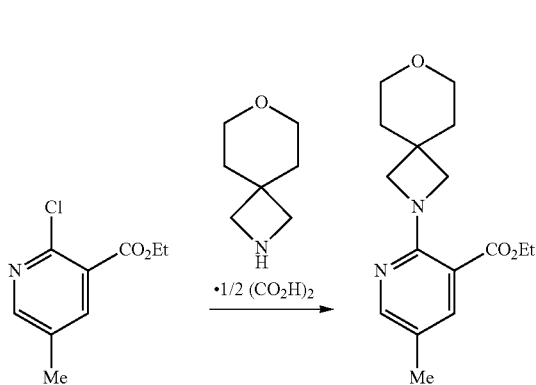 [SMILES: CCOC(=O)c1cc(C)cnc1Cl ; C1CC2(CCO1)CNC2 ; CCOC(=O)c1cc(C)cnc1N1CC2(CCOCC2)C1]

A mixture of ethyl 2-chloro-5-methylnicotinate (3.70 g, 18.5 mmol), 7-oxa-2-azaspiro[3.5] nonane hemi oxalate (9.57 g, 55.6 mmol) and DIPEA (19.4 mL, 111 mmol) in NMP (50 mL) was heated at 150° C. for 2 hr. After cooling to RT the crude mixture was poured into water (200 mL) and extracted with EtOAc (3×200 mL). The combined organic extracts were washed with brine (2×100 mL), and then dried and evaporated in vacuo to afford the title compound (4.81 g, g, 88% yield); R$^t$ 1.32 min; m/z 291 (M+H)$^+$ (ES+); $^1$H NMR δ: 1.29 (3H, t), 1.67 (4H, br t), 2.18 (3H, s), 3.52 (4H, br t), 3.67 (4H, s), 4.25 (2H, q), 7.74 (1H, apparent dd), 8.12 (1H, apparent dd).

5-Methyl-2-(7-oxa-2-azaspiro[3.5]nonan-2-yl)nicotinic Acid: Intermediate (VI)

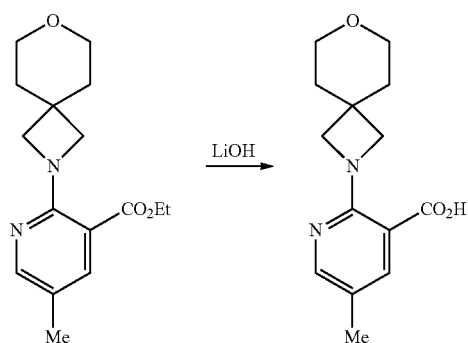 [SMILES: CCOC(=O)c1cc(C)cnc1N1CC2(CCOCC2)C1 ; "LiOH" ; Cc1cnc(N2CC3(CCOCC3)C2)c(C(=O)O)c1]

A mixture of ethyl 5-methyl-2-(7-oxa-2-azaspiro[3.5] nonan-2-yl)nicotinate (4.1 g, 14 mmol) and lithium hydroxide (0.50 g, 21 mmol) in THF:water (4:1, 50 mL) was heated at 50° C. for 18 hr and then evaporated in vacuo. The residue thus obtained was acidified to pH 4 by the addition of 1 M hydrochloric acid and the resulting mixture extracted with EtOAc (10×250 mL). The combined organic extracts were evaporated in vacuo to afford the title compound as a crystalline solid (3.4 g, 92% yield); R$^t$ 0.42 min; m/z 263 (M+H)$^+$ (ES$^+$); $^1$H NMR δ: 1.67 (4H, br t), 2.17 (3H, s), 3.52 (4H, br t), 3.69 (4H, s), 7.74 (1H, apparent dd), 8.09 (1H, apparent dd), 12.69 (1H, br).

1-(4-Nitrobenzoyl)-1,2,3,4-tetrahydro-5H-benzo[b]azepin-5-one

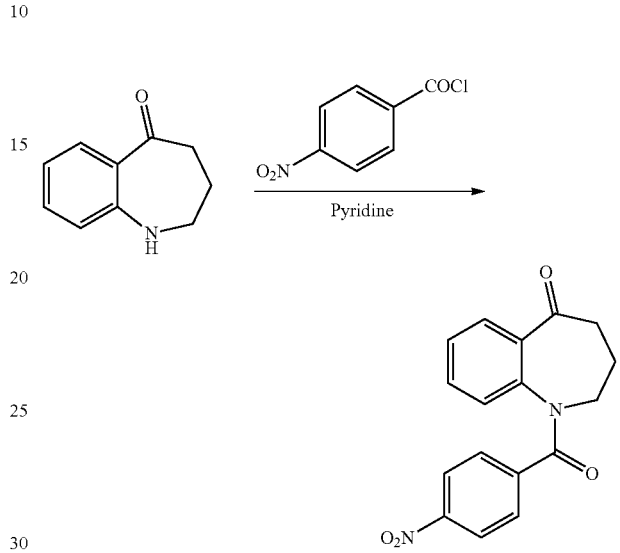

To a solution of 1,2,3,4-tetrahydro-benzo[b]azepin-5-one (25.0 g, 155 mmol) in pyridine (124 mL) at RT was added dropwise a solution of 4-nitrobenzoyl chloride (57.6 g, 310 mmol) in MeCN (124 mL). The resulting mixture was stirred at RT for 16 hr and was then quenched carefully with water (50 mL) and extracted with EtOAc (100 mL). The organic extracts were washed sequentially with sat aq NaHCO$_3$ (100 mL), sat aq NH$_4$Cl (2×100 mL), water (100 mL), brine (100 mL), and finally with 1 M hydrochloric acid (2×100 mL), dried and the volatiles evaporated in vacuo. The crude solid thus obtained was slurried with MeOH (300 mL) and was collected by filtration and dried to afford the title compound as a light yellow solid (44.8 g, 93% pure by HPLC, 93% yield); R$^t$ 1.92 min; m/z 311 (M+H)$^+$ (ES$^+$). This material was used in the subsequent step without additional purification.

5-Chloro-1-(4-nitrobenzoyl)-2,3-dihydro-1H-benzo[b]azepine-4-carbaldehyde

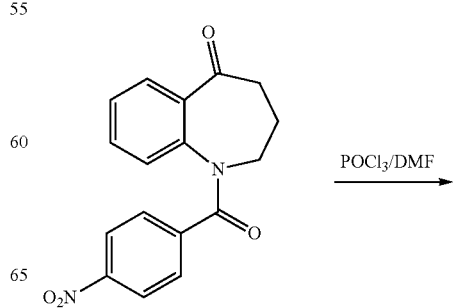

-continued

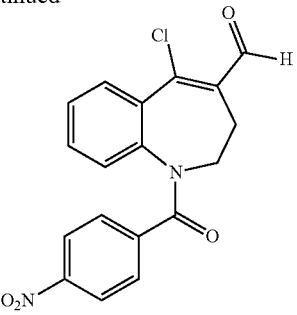

To neat DMF (236 mL) at 0° C. was added dropwise phosphoryl trichloride (15.8 mL, 170 mmol) and the resulting mixture treated with a solution of 1-(4-nitrobenzoyl)-1,2,3,4-tetrahydro-5H-benzo[b]azepin-5-one (44.8 g, 141 mmol) in DMF (141 mL) [the latter obtained by heating a suspension at 90° C. until full dissolution of the solid had occurred and the solution added whilst still hot] whilst maintaining the internal temp between 0-5° C. The reaction mixture was stirred at 0° C. for 15 min, then allowed to attain RT for 30 min and afterwards was heated at 80° C. for 72 hr. The resulting mixture was cooled to RT and was partitioned between EtOAc (500 mL) and sat aq NaOAc (500 mL). The aq layer was separated and was washed with EtOAc (2×500 mL). The combined organic extracts were washed with brine (8×300 mL), and then dried and evaporated in vacuo to give a brown solid. The crude product thus obtained was slurried with MeOH (300 mL) and was collected by filtration and dried to afford the title compound as a yellow solid (25.8 g, 88% pure by HPLC, 51% yield); R$^t$ 2.28 min; m/z 357 (M+H)$^+$ (ES$^+$). This material was used in the subsequent step without additional purification.

Ethyl 6-(4-nitrobenzoyl)-5,6-dihydro-4H-benzo[b]thieno[2,3-d]azepine-2-carboxylate: Intermediate (VIIIa)

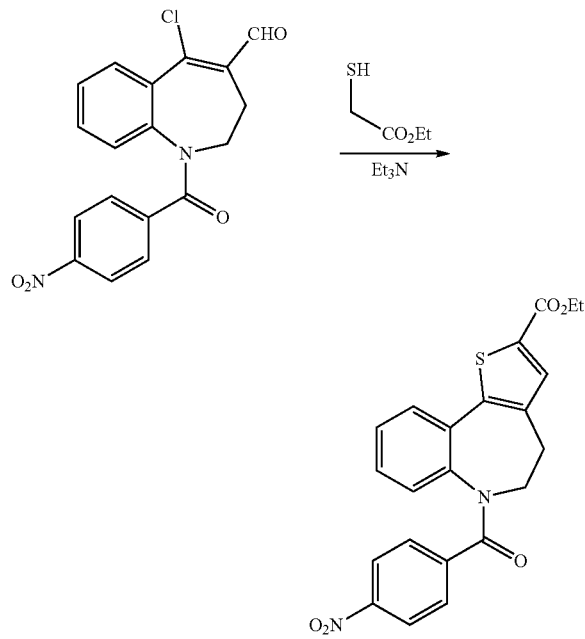

To a solution of 5-chloro-1-(4-nitrobenzoyl)-2,3-dihydro-1H-benzo[b]azepine-4-carbaldehyde (36.6 g, 89.0 mmol) in pyridine (260 mL) at RT was added ethyl 2-mercaptoacetate (18.6 mL, 170 mmol) followed by triethylamine (81.0 mL). The reaction mixture was heated at 70° C. for 1 hr, and at 118° C. for 2 hr and was then cooled to RT. The white precipitate that formed was removed by filtration and the filtrate concentrated in vacuo. The resulting residue was taken up in DCM (100 mL) and was washed with water (100 mL) and then with 1 M hydrochloric acid (70 mL). The organic extracts were dried and evaporated in vacuo. The crude solid thus obtained was slurried with MeOH (150 mL), collected by filtration and dried to afford the title compound as a yellow solid (34.2 g, 84% yield); R$^t$ 2.65 min; m/z 423 (M+H)$^+$ (ES$^+$); $^1$H NMR δ: 1.32 (3H, t), 3.09-3.17 (1H, m), 3.28-3.41 (assume 2H, obscured by solvent), 4.33 (2H, q), 4.83-4.92 (1H, m), 6.96 (1H, br d), 7.10 (1H, td), 7.24 (2H, br d), 7.28 (1H, td), 7.78-7.81 (2H, over-lapping s and dd), 8.06 (2H, br d).

6-(4-Nitrobenzoyl)-5,6-dihydro-4H-benzo[b]thieno[2,3-d]azepine-2-carboxylic Acid: Intermediate (VII)

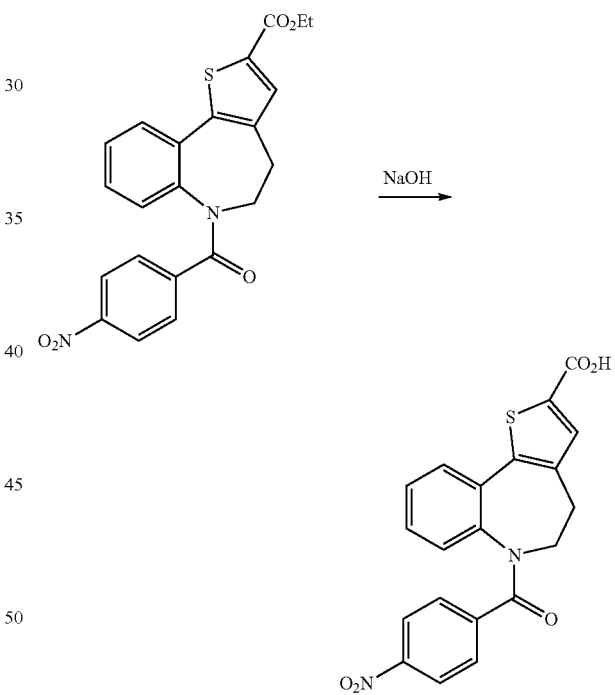

To a solution of ethyl 6-(4-nitrobenzoyl)-5,6-dihydro-4H-benzo[b]thieno[2,3-d]azepine-2-carboxylate (1.50 g, 3.55 mmol) in a mixture of THF:MeOH (1:1, 36 mL) was added 2 M aq NaOH (9.0 mL) and the mixture heated at 50° C. for 2 hr. After cooling to RT the mixture was partitioned between EtOAc (200 mL) and water (200 mL). The aq layer was separated and was acidified to pH 3 by the addition of 1 M hydrochloric acid and then extracted with EtOAc (2×150 mL). Removal of the volatiles in vacuo afforded the title compound, as a yellow solid (1.44 g, 99% yield); R$^t$ 2.24 min; m/z 395 (M+H)$^+$ (ES$^+$); $^1$H NMR δ: 3.06-3.17 (1H, m), 3.27-3.40 (assume 2H, obscured by solvent), 4.83-4.92 (1H, m), 6.95 (1H, br d), 7.08 (1H, br t), 7.23-7.30

(3H, over-lapping br d and br t), 7.69 (1H, s), 7.78 (1H, dd), 8.06 (2H, br d), 13.33 (1H, br s).

Ethyl 6-(4-aminobenzoyl)-5,6-dihydro-4H-benzo[b]thieno[2,3-d]azepine-2-carboxylate: Intermediate (IXa)

Catalytic Reduction Method

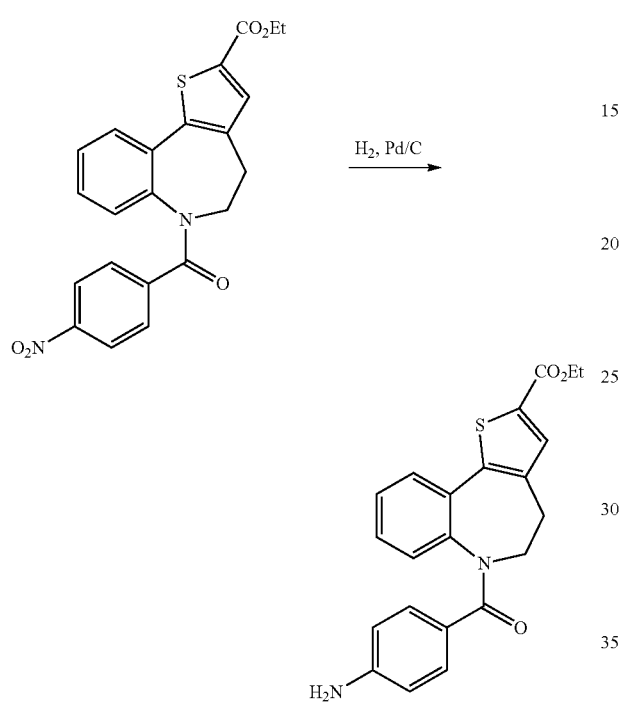

A solution of ethyl 6-(4-nitrobenzoyl)-5,6-dihydro-4H-benzo[b]thieno[2,3-d]azepine-2-carboxylate (1.00 g, 2.37 mmol) in a mixture of THF:EtOH (1:1, 100 mL) and 1 M hydrochloric acid (2.00 mL) was passed through a Thales H-cube (1.0 mL·min$^{-1}$, 25° C., 55 mm 10% Pd/C Cat-Cart, full hydrogen mode). The volatiles were removed in vacuo to afford the title compound (0.98 g, ~100% yield); R$^t$ 2.28 min; m/z 393 (M+H)$^+$ (ES$^+$). This material was used in the subsequent step without additional purification.

Dissolving Metal Reduction Method

To a suspension of iron powder (5.29 g, 94.7 mmol) and ethyl 6-(4-nitrobenzoyl)-5,6-dihydro-4H-benzo[b]thieno[2,3-d]azepine-2-carboxylate (8.00 g, 18.9 mmol) in IPA (80 mL) was added sat aq ammonium chloride (8.0 mL). The resulting mixture was stirred at 80° C. for 1 hr and was then filtered through celite. The celite pad was washed with MeOH (1.5 L) and combined filtrates were evaporated in vacuo. The resulting residue was triturated with water (400 mL) and with diethyl ether (400 mL) and was dried in vacuo to afford the title compound as a yellow solid (5.89 g, 88% pure by HPLC, 70% yield); R$^t$ 2.21 min; m/z 393 (M+H)$^+$ (ES$^+$). This material was used in subsequent steps without additional purification.

Ethyl 6-(4-(2-chloro-5-methylnicotinamido)benzoyl)-5,6-dihydro-4H-benzo[b]thieno[2,3-d]azepine-2-carboxylate: Intermediate (Xa)

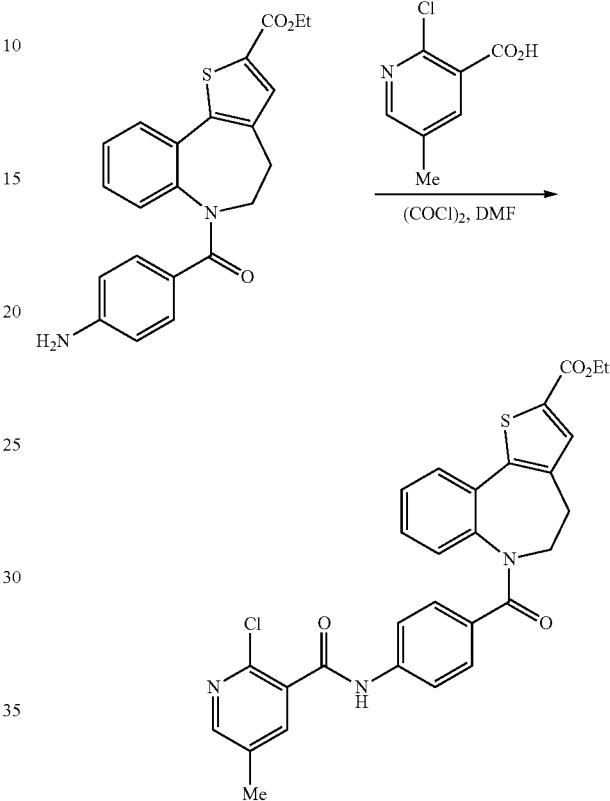

To a suspension of 2-chloro-5-methylnicotinic acid (2.49 g, 14.5 mmol) in DCM (50 mL) was added oxalyl chloride (4.24 mL, 48.4 mmol) and one drop of DMF. The resulting mixture was stirred at RT for 1 hr and was then evaporated in vacuo. The residue was taken up into DCM (25 mL) and added to a solution of ethyl 6-(4-aminobenzoyl)-5,6-dihydro-4H-benzo[b] thieno[2,3-d]azepine-2-carboxylate (3.80 g, 9.68 mmol) in pyridine (20 mL) at RT. The reaction mixture was maintained at RT for 1 hr and then quenched by the addition of water (100 mL) and extracted with EtOAc (100 mL). The aq layer was separated and was washed with EtOAc (2×100 mL). The combined organic extracts were washed with water (100 mL), evaporated in vacuo and the resulting solid triturated with water (200 mL). This sequence was repeated on the same scale to afford the title compound as a pale yellow solid (10.0 g, 89% pure by HPLC, 95% yield); R$^t$ 2.51 min; m/z 545/547 (M+H)$^+$ (ES$^+$). This material was used in subsequent steps without additional purification.

19

N-(2-fluoro-6-methylphenyl)-6-(4-nitrobenzoyl)-5,6-dihydro-4H-benzo[b]thieno[2,3-d] azepine-2-carboxamide

20

Ethyl 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylate Method 1: Acylation of Aniline (IXa) with 2-aminonicotinc Acid (VI)

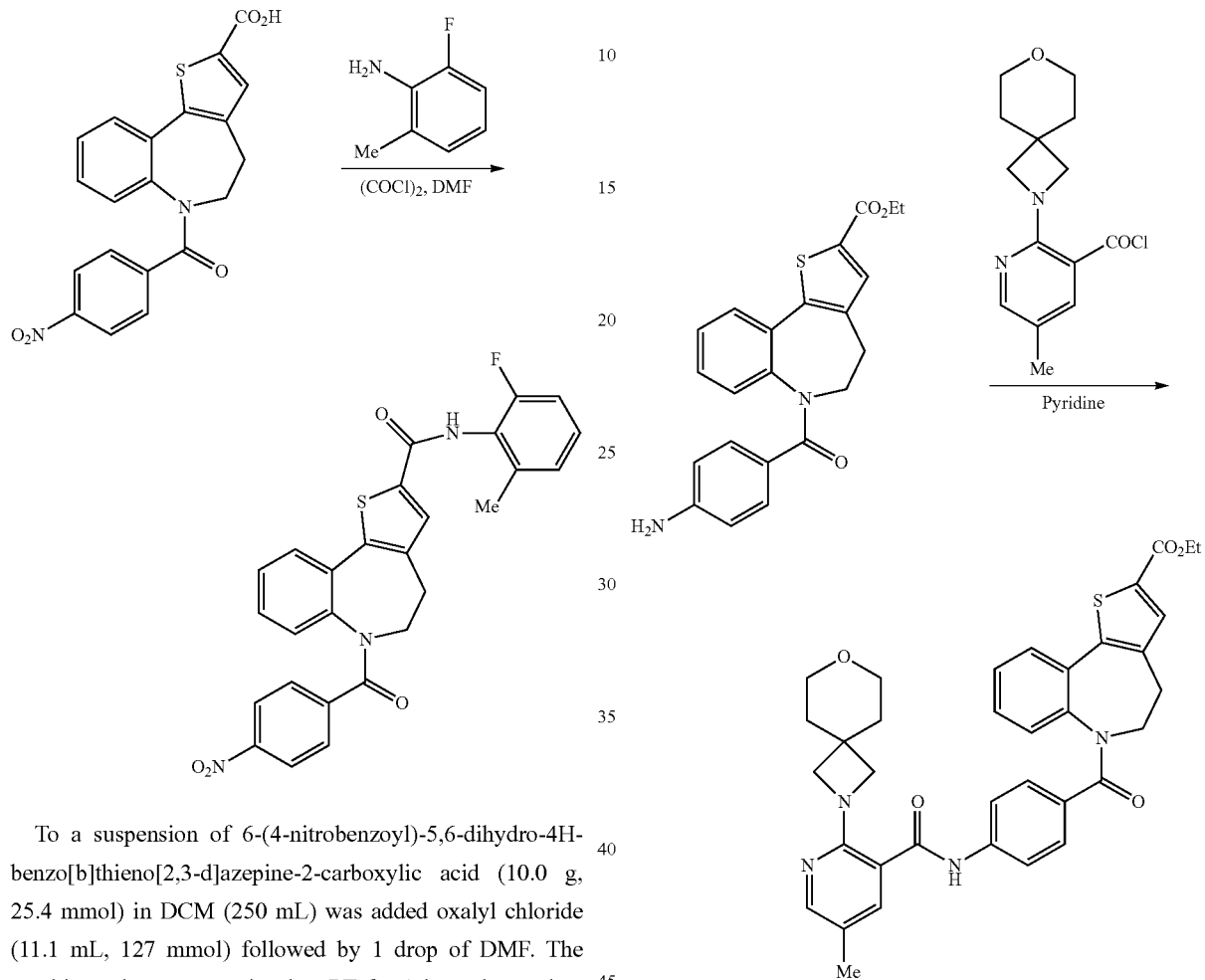

To a suspension of 6-(4-nitrobenzoyl)-5,6-dihydro-4H-benzo[b]thieno[2,3-d]azepine-2-carboxylic acid (10.0 g, 25.4 mmol) in DCM (250 mL) was added oxalyl chloride (11.1 mL, 127 mmol) followed by 1 drop of DMF. The resulting mixture was stirred at RT for 1 hr and was then evaporated in vacuo. The residue thus obtained was taken up into DCM (100 mL) and to this solution was added a solution of 2-fluoro-6-methylaniline (6.35 g, 50.7 mmol) in pyridine (100 mL). The mixture was stirred at RT for 1 hr and was then evaporated in vacuo. The residue was taken up into EtOAc (500 mL) and the solution was washed with 1 M hydrochloric acid (2×100 mL), followed by sat aq NaHCO$_3$ (100 mL) and then dried and evaporated in vacuo. This same procedure was repeated three times with additional 6-(4-nitrobenzoyl)-5,6-dihydro-4H-benzo[b]thieno[2,3-d]azepine-2-carboxylic acid (12.0 g, 30.4 mmol) to afford the title compound as a pale yellow solid (51.1 g, 93% pure by HPLC, 87% yield); R$^t$ 2.46 min; m/z 502 (M+H)$^+$ (ES$^+$). This material was used in the subsequent step without additional purification.

To a suspension of 5-methyl-2-(7-oxa-2-azaspiro[3.5]nonan-2-yl)nicotinic acid (2.21 g, 8.41 mmol) in DCM (50 mL) was added oxalyl chloride (0.80 mL, 9.17 mmol) followed by 1 drop of DMF. The resulting mixture was stirred at RT for 1 hr and then a second portion of oxalyl chloride (0.80 mL, 9.17 mmol) and of DMF (1 drop) were added. After a further 30 min the mixture was evaporated in vacuo and the residue thus obtained taken up into DCM (50 mL) and added to a solution of ethyl 6-(4-aminobenzoyl)-5,6-dihydro-4H-benzo[b]thieno[2,3-d]azepine-2-carboxylate (3.00 g, 7.64 mmol) in pyridine (20 mL). The resulting mixture was stirred at RT for 1 hr, then diluted with water (100 mL) and passed through a phase separator. The organic phase was evaporated in vacuo and the residue obtained purified by flash column chromatography (SiO$_2$, 80 g, 0-100% EtOAc in isohexane, gradient elution). The pale orange residue that was isolated was triturated with acetonitrile (2×20 m L) and the solid that formed was collected by filtration and dried to afford the title compound as a white solid (2.78 g, 94% pure by HPLC, 57% yield); R$^t$ 1.95 min; m/z 637 (M+H)$^+$ (ES$^+$); $^1$H NMR δ: 1.32 (3H, t), 1.62 (4H, br t), 2.16 (3H, s), 3.06-3.38 (assume 3H, obscured by solvent), 3.45 (4H, br t), 3.60 (4H, s), 4.32 (2H, q), 4.85-4.95 (1H, br), 6.88 (1H, br d), 6.99 (2H, br d), 7.14 (1H, br t), 7.29 (1H, td), 7.45-7.53 (3H, over-lapping m), 7.79 (1H, s), 7.82 (1H, dd), 8.04 (1H, apparent dd), 10.37 (1H, s).

Method 2: Displacement of 2-halonicotinamide (Xa) with a 7-oxa-2-azaspiro[3.5]nonane 6-(4-(5-Methyl-2-(7-oxa-2-azaspiro[3.5]nonan-2-yl) nicotinamido)benzoyl)-5,6-dihydro-4H-benzo[b] thieno[2,3-d]azepine-2-carboxylic Acid: Intermediate (II)

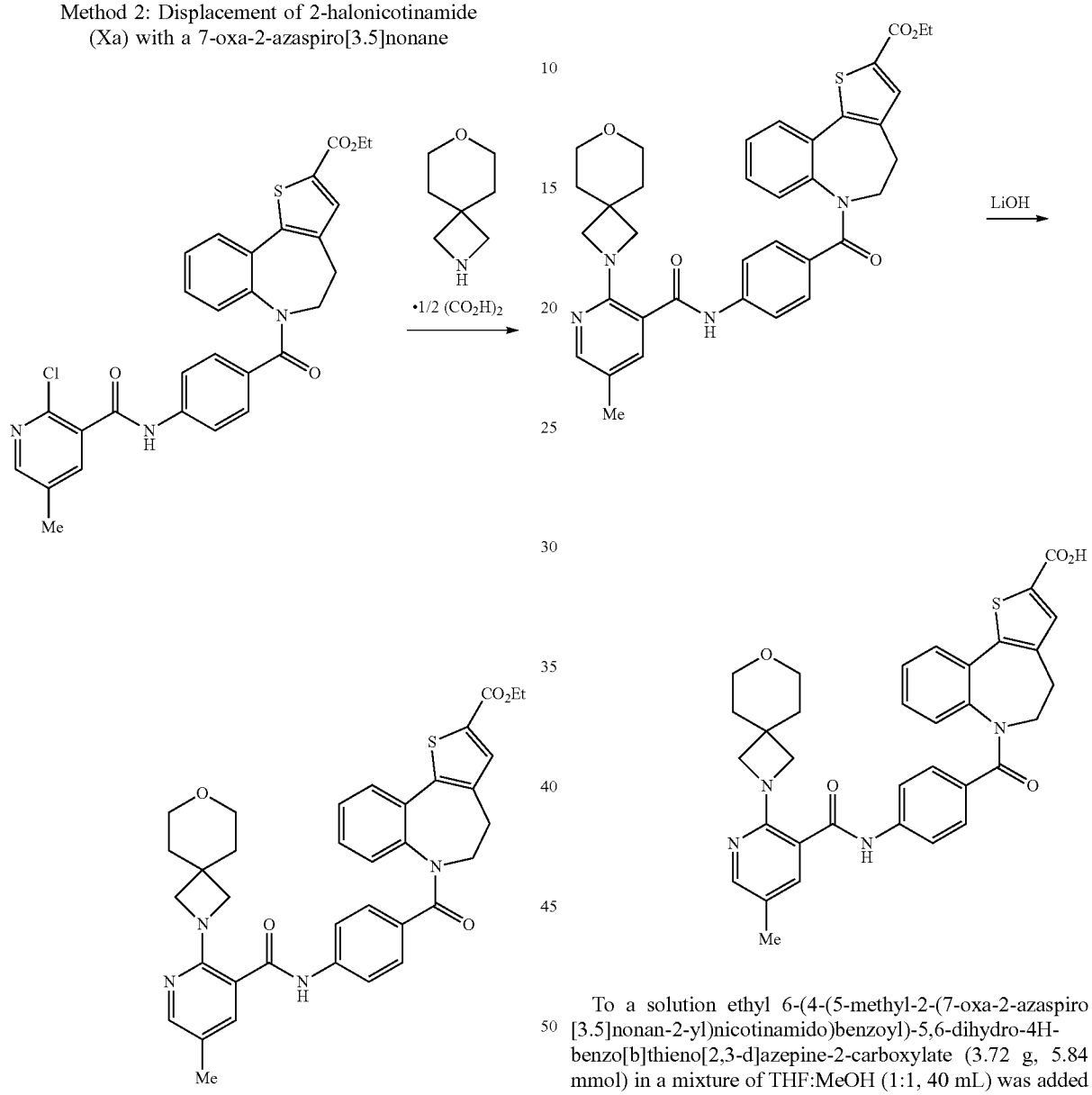

A suspension of ethyl 6-(4-(2-chloro-5-methylnicotinamido)benzoyl)-5,6-dihydro-4H-benzo[b]thieno[2,3-d] azepine-2-carboxylate (4.97 g, 9.10 mmol) and 7-oxa-2-azaspiro[3.5] nonane hemi oxalate (5.93 g, 27.3 mmol) in NMP (23 mL) and Et$_3$N (7.61 mL, 54.6 mmol) was heated at 150° C. for 7.5 hr and then cooled to RT and left to stand for 60 hr. Water (400 mL) was added and the resulting precipitate was collected by filtration. The solid thus obtained was purified by flash column chromatography (SiO$_2$, 120 g, 0-30% THF in DCM, gradient elution) to afford the title compound as a pale yellow solid (3.72 g, 64% yield); R$^t$ 1.94 min; m/z 637 (M+H)$^+$ (ES$^+$).

To a solution ethyl 6-(4-(5-methyl-2-(7-oxa-2-azaspiro [3.5]nonan-2-yl)nicotinamido)benzoyl)-5,6-dihydro-4H-benzo[b]thieno[2,3-d]azepine-2-carboxylate (3.72 g, 5.84 mmol) in a mixture of THF:MeOH (1:1, 40 mL) was added a solution of lithium hydroxide (700 mg, 29.2 mmol) in water (40 mL). The reaction mixture was heated to 50° C. for 1 hr and was then cooled to RT. The volatiles were removed in vacuo and the remaining aq solution was diluted with water and sonicated until the resulting precipitate dissolved. This mixture was neutralised by the addition of 1 M hydrochloric acid and the resulting solid collected by filtration and dried in vacuo to afforded the title compound as an off-white solid (3.27 g, 92% yield); R$^t$ 1.64 min; m/z 609 (M+H)$^+$ (ES$^+$); $^1$H NMR δ: 1.62 (4H, br t), 2.16 (3H, s), 3.00-3.51 (assume 8H, obscured by solvent), 3.60 (4H, s), 4.82-4.96 (1H, br), 6.86 (1H, br d), 6.99 (2H, br d), 7.11 (1H, br t), 7.28 (1H, td), 7.46-7.54 (3H, over-lapping m), 7.62 (1H, s), 7.78 (1H, dd), 8.03 (1H, dd), 10.38 (1H, s).

6-(4-(2-Chloro-5-methylnicotinamido)benzoyl)-N-(2-fluoro-6-methylphenyl)-5,6-dihydro-4H-benzo[b]thieno[2,3-d]azepine-2-carboxamide: Intermediate (IIIa)

6-(4-aminobenzoyl)-N-(2-fluoro-6-methylphenyl)-5,6-dihydro-4H-benzo[b]thieno[2,3-d]azepine-2-carboxamide: Intermediate (IV)

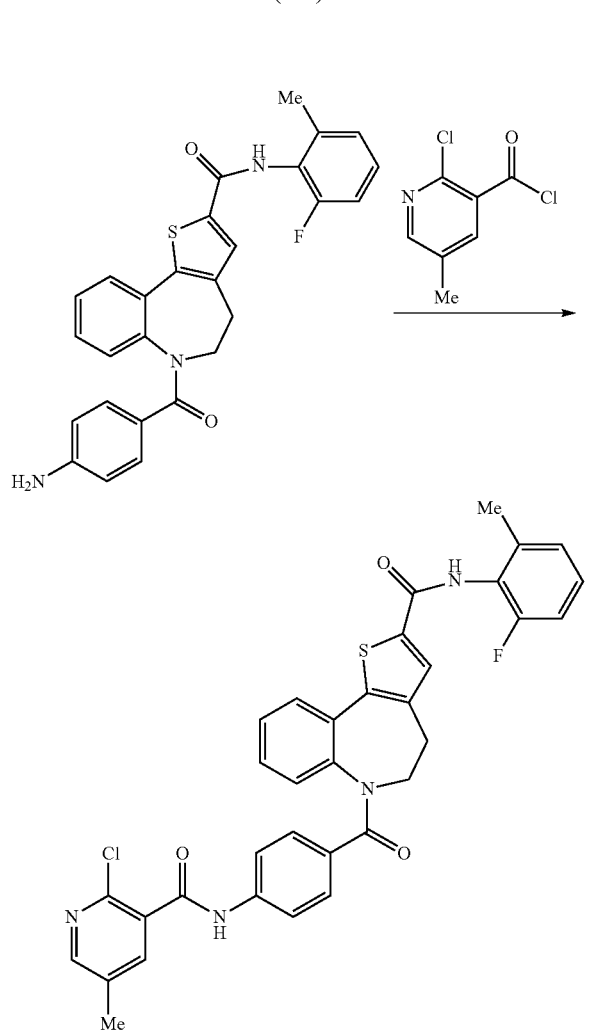

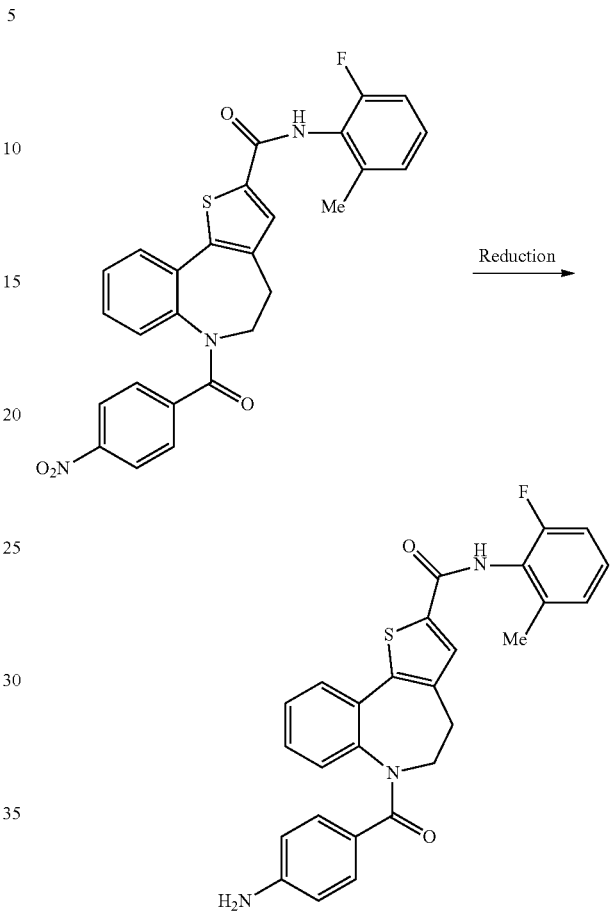

A solution of 2-chloronicotinoyl chloride (1.21 g, 3.36 mmol) in DCM (10 mL) was added to a stirred solution of 6-(4-aminobenzoyl)-N-(2-fluoro-6-methylphenyl)-5,6-dihydro-4H-benzo[b] thieno[2,3-d]azepine-2-carboxamide (2.00 g, 4.24 mmol) in pyridine (10 mL). The reaction mixture was stirred at RT for 1 hr and was then poured into water (100 mL) and extracted into EtOAc (2×50 mL) The combined organics were evaporated in vacuo and the resulting solid was slurried in EtOAc (50 mL) and collected by filtration. The above procedure was repeated three times, on an increasingly greater scale, using 5.0, 15.0 and finally 18.0 g of the aniline starting material. All four batches were combined by dissolving them in DCM (300 mL). The solvent was evaporated in vacuo to give the title compound as a white solid (40.3 g, 75% yield); $R^t$ 2.39 min; m/z 625 $(M+H)^+$ $(ES^+)$; $^1H$ NMR δ: 2.26 (3H, s), 2.32 (3H, s), 3.09-3.33 (assume 3H, obscured by solvent), 4.83-5.03 (1H, m), 6.86 (1H, d), 7.04 (2H, d), 7.09-7.19 (3H, m), 7.22-7.34 (2H, m), 7.51 (2H, d), 7.83 (1H, dd), 7.91 (1H, d), 7.96 (1H, s), 8.36 (1H, dd), 10.04 (1H, s), 10.71 (1H, s).

Method 1: Dissolving Metal Reduction

To a solution of N-(2-fluoro-6-methylphenyl)-6-(4-nitrobenzoyl)-5,6-dihydro-4H-benzo[b] thieno[2,3-d]azepine-2-carboxamide (5.00 g, 9.97 mmol) in EtOH (100 mL) was added ammonium chloride (5.33 g, 100 mmol), water (20 mL) and then iron powder (2.78 g, 49.8 mmol). The resulting mixture was stirred at reflux for 1 hr and was then filtered through celite. The celite pad was washed with EtOH (50 mL) and the combined filtrates were evaporated in vacuo. The resulting residue was taken up into EtOAc (200 mL), washed with water (2×100 mL) and was then dried and evaporated in vacuo. This procedure was repeated three times with additional N-(2-fluoro-6-methylphenyl)-6-(4-nitrobenzoyl)-5,6-dihydro-4H-benzo[b]thieno [2,3-d]azepine-2-carboxamide (15.0 g, 29.9 mmol) and the solids that were obtained were combined and triturated with $Et_2O$ (200 mL) to afford the title compound as a pale yellow solid (41.1 g, 87% yield); $R^t$ 2.12 min; m/z 472 $(M+H)^+$ $(ES^+)$; $^1H$ NMR δ: 2.25 (3H, s), 3.02-3.30 (3H, br), 4.85-5.05 (1H, br), 5.51 (2H, s), 6.27 (2H, d), 6.75 (2H, d), 6.80 (1H, d), 7.10-7.15 (3H, over-lapping m), 7.24-7.30 (2H, over-lapping m), 7.81 (1H, dd), 7.93 (1H, s), 10.02 (1H, s).

Method 2: Catalytic Hydrogenation

To a solution of N-(2-fluoro-6-methylphenyl)-6-(4-nitrobenzoyl)-5,6-dihydro-4Hbenzo[b] thieno[2,3-d]azepine- 2-carboxamide (100 mg, 0.199 mmol) in THF (4.0 mL) was added 5% Pd/C paste (58 wt % water, 21.0 mg, 0.100 mmol) and the mixture stirred under 5 bar of hydrogen for 18 hr. Upon competition of the reaction the mixture was passed through a Agilent 0.45 μm syringe filter and filtrate evaporated in vacuo to afford the title compound (91.0 mg, 97% yield); $R^t$ 2.13 min; m/z 472 (M+H)$^+$ (ES$^+$).

Preparation of N-(2-Fluoro-6-methylphenyl)-6-(4-(5-methyl-2-(7-oxa-2-azaspiro[3.5] nonan-2-yl)nicotinamido)benzoyl)-5,6-dihydro-4H-benzo[b]thieno[2,3-d]azepine-2-carboxamide: Compound (I)

Route 1: Amide Coupling of the Thiophene Carboxylic Acid (II) with 2-fluoro-6-methylaniline

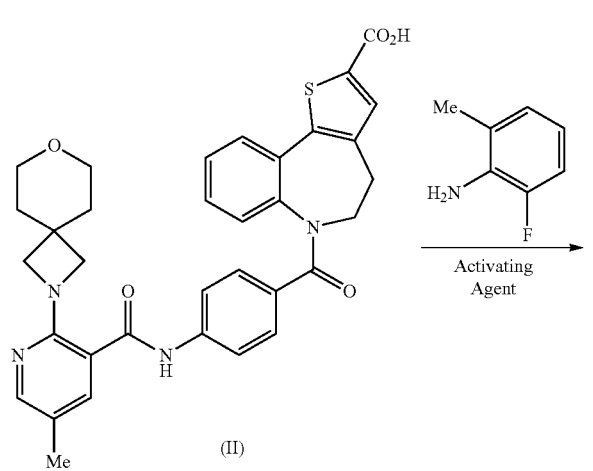

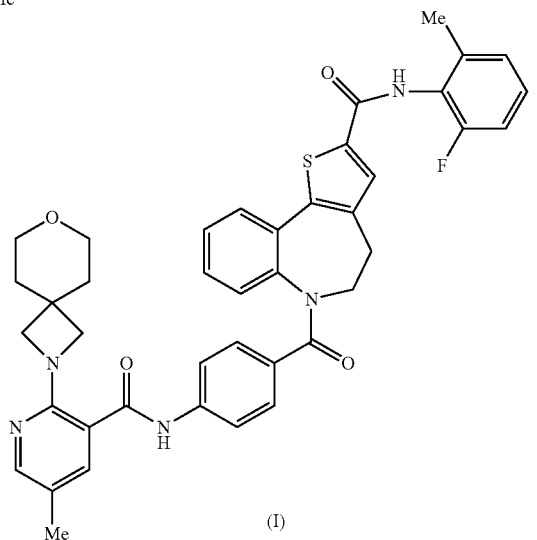

To a solution of 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylic acid (400 mg, 0.657 mmol) in DCM (40 mL) was added 1-chloro-N,N,2-trimethylprop-1-en-1-amine (174 μL, 1.31 mmol). The reaction was stirred at RT for 1.5 hr and was then concentrated in vacuo. The residue was taken up in DCM (40 mL) and an aliquot of this solution (5.0 mL, 0.080 mmol) was added to 2-fluoro-6-methylaniline (100 mg, 0.797 mmol) and the reaction mixture stirred at RT for 3 days. The volatiles were evaporated in vacuo and the resulting residue was purified by preparative HPLC to afford Compound (I), as an off-white solid (14 mg, 23% yield); $R^t$ 1.85 min; m/z 716 (M+H)+(ES$^+$); $^1$H NMR δ: 1.62 (4H, br t), 2.17 (3H, s), 2.26 (3H, s), 3.14-3.37 (assume 3H, obscured by solvent), 3.46 (4H, br t), 3.60 (4H, s), 4.90-4.98 (1H, br), 6.88 (1H, br d), 7.02 (2H, br d), 7.10-7.16 (3H, over-lapping m), 7.25-7.31 (2H, over-lapping m), 7.48 (1H, d), 7.52 (2H, br d), 7.82 (1H, dd), 7.95 (1H, s), 8.04 (1H, dd), 10.03 (1H, s), 10.37 (1H, s).

Route 2: S$_N$Ar displacement of the chloronicotinamide (III) with 7-oxa-2-azaspiro[3.5]nonane

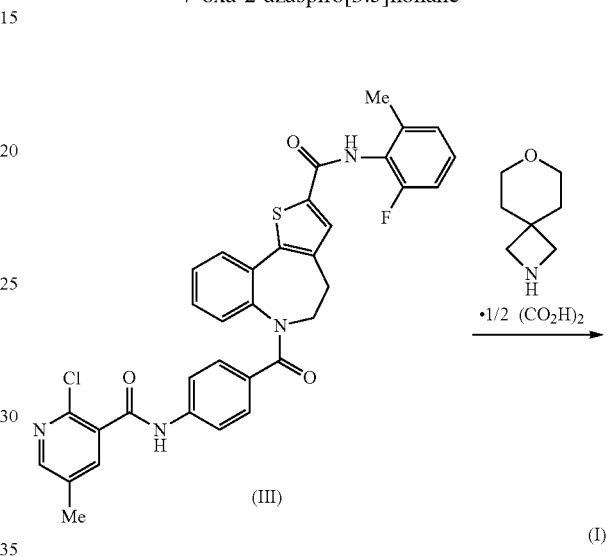

To a solution of 6-(4-(2-chloro-5-methylnicotinamido)benzoyl)-N-(2-fluoro-6-methylphenyl)-5,6-dihydro-4H-benzo[b]thieno[2,3-d]azepine-2-carboxamide (10.0 g, 16.0 mmol) and 7-oxa-2-azaspiro[3.5]nonane hemi oxalate (10.4 g, 48.0 mmol) in NMP (125 mL) was added triethylamine (13 mL, 96 mmol) and the reaction mixture heated at 145° C. for 7 hr. After cooling to RT the mixture was poured into water (800 mL) and the resulting solids were collected by filtration, washed with water (2×100 mL) and then taken up in DCM (400 mL). The solution was washed with water (100 mL), dried over sodium sulphate and evaporated in vacuo. The solid residue was purified by flash column chromatography (SiO$_2$, 220 g, 20-100% EtOAc in diethyl ether, gradient elution) to afford the title compound as a white solid. This procedure was repeated on additional 5 and 10 g batches of the chloronicotinamide starting material. The three product batches were combined by dissolution in EtOAc (500 mL) and evaporation of the solvent in vacuo. The resulting solid was triturated with diethyl ether (200 mL) and the solid collected by filtration and dried to afford the title compound, Compound (I) as a white solid (24 g, 82% yield); $R^t$ 1.88 min; m/z 716 (M+H)$^+$ (ES$^+$).

Route 3: Amide Coupling of the Aniline (IV) with the 2-aminonicotinic Acid (VI)

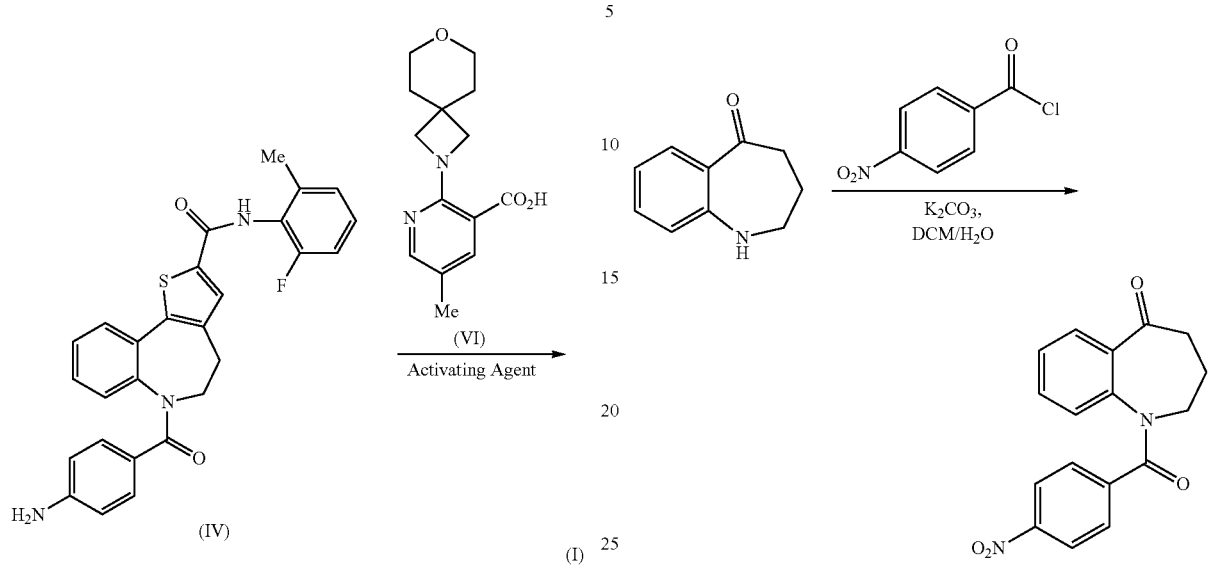

1-(4-Nitrobenzoyl)-1,2,3,4-tetrahydro-5H-benzo[b]azepin-5-one

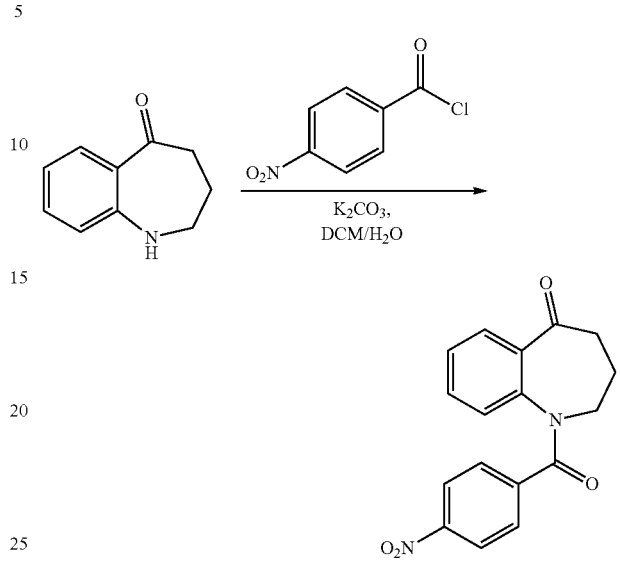

To a solution of 5-methyl-2-(7-oxa-2-azaspiro[3.5]nonan-2-yl)nicotinic acid (83 mg, 0.32 mmol) in DCM (5.0 mL) was added 1-chloro-N,N,2-trimethylprop-1-en-1-amine (37 μL, 0.28 mmol). The mixture was stirred at RT for 15 min and was then added to a solution of 6-(4-aminobenzoyl)-N-(2-fluoro-6-methyl phenyl)-5,6-dihydro-4H-benzo[b]thieno[2,3-d]azepine-2-carboxamide (100 mg, 0.21 mmol) in pyridine (5.0 mL). The reaction mixture was stirred for a further 1 hr and concentrated in vacuo. The residue was triturated with water (20 mL) and the resulting buff solid was collected by filtration and was purified by flash column chromatography (SiO$_2$, 12 g, 0-10% MeOH in DCM, gradient elution) to afford Compound (I), as a white solid (55 mg, 36% yield); R$^t$ 1.88 min; m/z 716 (M+H)$^+$ (ES$^+$).

Scale-Up of the Preparation of Compound (I) by Route 2

The synthetic methodology described above for Route 2, has been successfully exploited to prepare the compound of the present invention on a scale of >0.5 kg. Analytical and spectroscopic methods pertaining to this campaign are described below.

Analytical and Spectroscopic Methods

Reverse Phase HPLC Conditions for LCMS Analysis:

CORTECS C18$^+$4.6×150 mm column; 2.7 μm (Ex. Waters #186007408) at 40° C.; flow rate 1.0 mL·min$^{-1}$ eluted with a purified H$_2$O-MeCN gradient containing 0.1% formic acid over 25 min employing UV detection at 310 nm. Injection volume 5 μL. Gradient information: 0-15 min, ramped from 95% H$_2$O-5% MeCN to 5% H$_2$O-95% MeCN; 15-25 min, held at 5% H$_2$O-95% MeCN.

$^1$H NMR Spectroscopy:

Spectra were acquired using a JOEL ECX 400 MHz spectrometer. Residual undeuterated solvent was used as reference and samples were run in DMSO-d$_6$.

To a solution of 1,2,3,4-tetrahydrobenzazepin-5-one (2670 g, 16.6 mol) in DCM (23.2 L) was added a 30% w/v aq solution of K$_2$CO$_3$ (15.2 L). 4-Nitrobenzoyl chloride (3105 g, 16.7 mol) was added portion-wise over 15 min maintaining an internal temp of <25° C. The reaction was stirred at 18-25° C. for 18 hr at which point TLC (50% v/v ethyl acetate in heptane) indicated the reaction was incomplete. Additional 4-nitrobenzoyl chloride (167 g, 0.9 mol) was added and the reaction stirred for a further 1.5 hr after which TLC indicated the reaction was complete. The phases were separated and the organics were added to a solution of 2M NaOH (10 L) and stirred for 2 hr. The phases were separated and the organics were washed with water (2×5 L), dried over MgSO$_4$ and filtered. The pad was washed with DCM (4 L) and the combined organics were evaporated in vacuo. The resulting solid was dried in vacuo at 45° C. for 24 hr to afford the title compound as a light beige solid (4998 g, 97% active yield; HPLC purity 96.2%, NMR purity >95%); R$^t$ 10.09 min; m/z 311.1 (M+H)$^+$ (ES$^+$).

5-Chloro-1-(4-nitrobenzoyl)-2,3-dihydro-1H-benzo[b]azepine-4-carbaldehyde

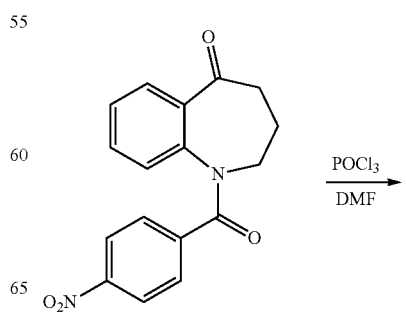

-continued

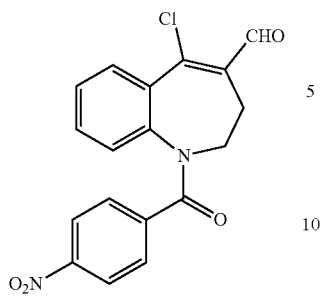

A 50 L vessel charged with DMF (10.0 L) was cooled to 0° C. and was treated dropwise over 1 hr with phosphoryl chloride (1802 mL, 19.33 mol), whilst maintaining the internal temp below 5° C. (an exotherm from 0-5° C. was observed) and was then stirred for 30 min at 0-5° C. A solution of 1-(4-nitrobenzoyl)-1,2,3,4-tetrahydro-5H-benzo[b]azepin-5-one (5000 g, 16.11 mol) in DMF (10.0 L), prepared by dissolution at 70° C., was then added whilst warm (to avoid precipitation) to the phosphoryl chloride/DMF solution via vacuum transfer over 30 min, maintaining the batch temp between 0-10° C. On completion of the addition, the reaction was stirred under nitrogen for 30 min at 0-5° C. and then at 80° C. for 18 hr, at which time HPLC analysis showed consumption of the starting material was complete. The reaction mixture was cooled to 40° C. and was divided into two equal portions, both of which were worked up in the same manner, as follows. The first portion was concentrated in vacuo to approximately half of its original volume (~7 L) and was then added to sat aq NaOAc (34.0 L), pre-cooled to 10° C., over 2 hr (an exotherm from 20-30° C. was observed). After stirring for 15 min at 20° C. the mixture was extracted with DCM (27.2 L) and the phases were separated. The aq layer was back-extracted with DCM (27.2 L), and the phases were separated. The combined organic extracts were washed with water (2×40 L) then dried over MgSO$_4$ (4.0 kg), filtered, and the filtrate concentrated. The same work-up procedure was repeated on the second portion of the crude reaction mixture and combined with the first, to give the title compound as an oil (5119 g, 89% active yield, HPLC purity 87.6%, $^1$H NMR purity of 95%); R$^t$ 11.74 min; m/z 357.2 (M+H)$^+$ (ES$^+$).

Ethyl 6-(4-Nitrobenzoyl)-5,6-dihydro-4H-benzo[b]thieno[2,3-d]azepine-2-carboxylate

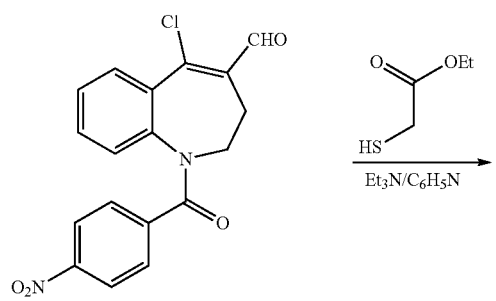

-continued

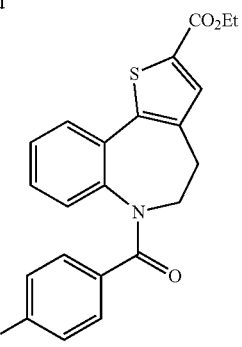

To a solution of 5-chloro-1-(4-nitrobenzoyl)-2,3-dihydro-1H-benzo[b]azepine-4-carbaldehyde (3418 g, 9.580 mol) in pyridine (15.83 L, 195.4 mol) at 10° C. under nitrogen was added ethyl-2-mercaptoacetate (1118 mL, 10.24 mol) dropwise over 30 min, whilst maintaining the internal temp below 20° C. (an exotherm from 10 to 15° C. was observed). The resulting solution was then treated dropwise with triethylamine (7531.51 mL, 54.03 mol) over 30 min, keeping the internal temp below 20° C. (no exotherm observed). The reaction mixture was stirred at 20° C. for 1 hr and then at 70° C. for 18 hr. After this time HPLC analysis revealed that consumption of the starting chloro enal was complete and the reaction was allowed to cool to 18-25° C.

The mixture was filtered (to remove insoluble salts), and the pad was washed with acetone (1.0 L). The combined filtrates were concentrated in vacuo to remove volatiles, and the residue taken up into DCM (11964 mL) and washed with water (7623 mL). The organic phase was separated and was washed with 1M hydrochloric acid (7623 mL) and then dried over MgSO$_4$. The inorganics were removed by filtration, washed with DCM (4.0 L) and the combined filtrates were evaporated in vacuo to an oily residue.

The residue was taken up into ethanol (20500 mL) and the solution was stirred at 60° C. for 1 hr and was then cooled to 18-25° C. and stirred at this temperature for 1 hr. The resulting solid was collected by filtration, washed with ethanol (13.8 L) and dried at 50° C. under vacuum, to afford the title compound (2939 g, 73% active yield, HPLC purity 96.9%, $^1$H NMR purity >97%); R$^t$ 13.85 min; m/z 423.2 (M+H)$^+$ (ES$^+$).

6-(4-Nitrobenzoyl)-5,6-dihydro-4H-benzo[b]thieno[2,3-d]azepine-2-carboxylic Acid

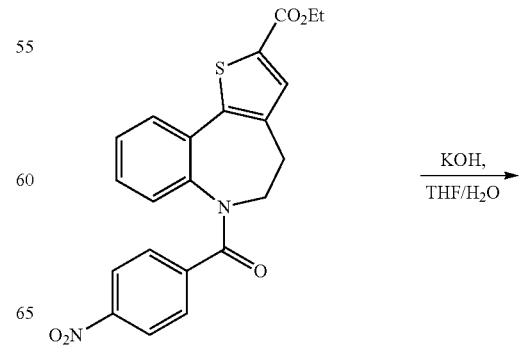

-continued

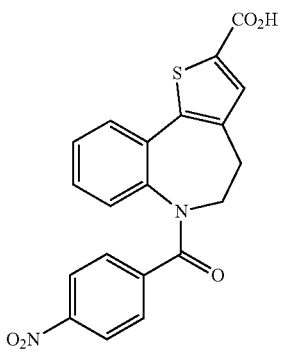

A 50 L vessel, was charged at 18-25° C. with a 1:1 mixture of THF and water (37.63 L) and ethyl 6-(4-nitrobenzoyl)-5,6-dihydro-4H-benzo[b]thieno[2,3-d]azepine-2-carboxylate (3763.7 g, 8.90 mol). To the resulting solution was added solid KOH (749.1 g, 13.35 mol) portion-wise, whilst keeping the internal temp below 25° C. (an exotherm from 20-22° C. was observed). The reaction was heated at 50° C. for 18 hr at which time H PLC analysis revealed that consumption of the starting material was complete. The reaction was allowed to cool to 18-25° C. and the organic solvent was removed in vacuo. The remaining aq solution was diluted with water (28.27 L) and then conc hydrochloric acid (1.25 L) was added slowly to the solution until pH 1 was attained (a 5° C. exotherm was observed, with moderate off-gassing). The resulting light tan suspension was filtered and the pad was washed with water (2×9.5 L). The solid was dried in an oven under vacuum at 50° C. to afford the title compound (3185.5 g, 91% active yield, HPLC purity 98.0%, $^1$H NMR assay 91.0%); R$^t$ 11.11 min; m/z 395.2 (M+H)$^+$ (ES$^+$).

N-(2-Fluoro-6-methylphenyl)-6-(4-nitrobenzoyl)-5,6-dihydro-4H-benzo[b]thieno[2,3-d] azepine-2-carboxamide

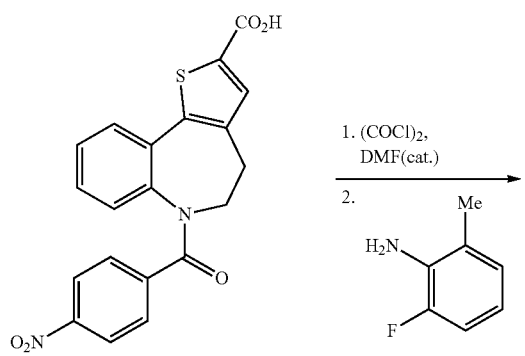

-continued

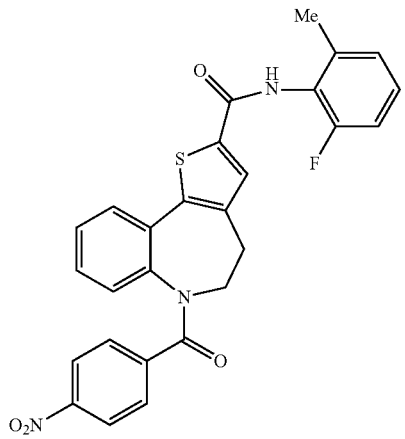

A suspension in DCM (15.6 L), of 6-(4-nitrobenzoyl)-5,6-dihydro-4H-benzo[b]thieno[2,3-d] azepine-2-carboxylic acid (1714 g, 1560 g active material, 3.955 mol) was placed under a nitrogen atmosphere and DMF (6.2 mL, 79.1 mmol) was added to the mixture. Oxalyl chloride (690 mL, 7.91 mol) was then added slowly over 40 min in order to control gas evolution (an exotherm from 16.9-18.3° C. was observed) and the reaction mixture was stirred at 18-25° C. overnight. TLC analysis (8% methanol in DCM) indicated that some of the thiophene carboxylic acid starting material remained and additional oxalyl chloride (300 mL, 3.44 mol) was added to the mixture. After stirring at 18-25° C. for 3 hr the reaction was complete and the resulting mixture was concentrated in vacuo to provide 6-(4-nitrobenzoyl)-5,6-dihydro-4H-benzo[b]thieno[2,3-d]azepine-2-carbonyl chloride as a dark yellow solid ($^1$H NMR indicated the presence of 15.4% DCM and 0.5% DMF).

The crude acid chloride so obtained was suspended in DCM (7.8 L) under a nitrogen atmosphere and was treated with pyridine (480 mL, 5.93 mol). 2-Fluoro-6-methylaniline (475 mL, 4.11 mol) was then added slowly over 15 min, with cooling from an ice/water bath, (resulting in an exotherm from 20.9-35.2° C.). The mixture formed a solution and was stirred at 18-25° C. overnight at which point the reaction was determined to be complete (HPLC 250 nm).

The resulting suspension was divided into two equal portions, each of which were diluted with water (7.8 L), stirred for 1 hr at 18-25° C. and then the solids collected by filtration. The two filter cakes were each washed with water (1.8 L) and with DCM (2×1.6 L) and combined. The solid was dried in an oven at 50° C. to provide the title compound as an off-white solid, (1573 g, 79% active yield, $^1$H NMR purity >95%, containing 1.98% DCM and 0.56% of pyridine.HCl); R$^t$ 12.76 min; m/z 502.4 (M+H)$^+$ (ES$^+$).

6-(4-Aminobenzoyl)-N-(2-fluoro-6-methylphenyl)-5,6-dihydro-4H-benzo[b]thieno[2,3-d] azepine-2-carboxamide; Intermediate (IV)

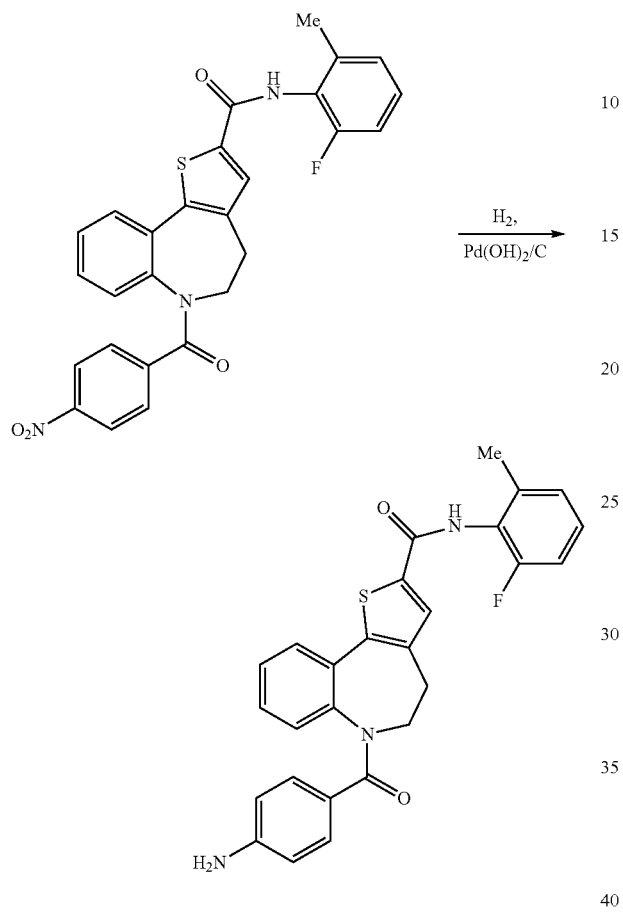

To a solution of N-(2-fluoro-6-methylphenyl)-6-(4-nitrobenzoyl)-5,6-dihydro-4H-benzo[b] thieno[2,3-d]azepine-2-carboxamide (80 g, 0.160 mol) in a mixture of DMF (240 mL) and 2-MeTHF (640 mL), under a nitrogen atmosphere, was added 20% Pd(OH)$_2$/C catalyst (8.0 g) and the mixture sparged with hydrogen and heated to 55° C. After sparging with hydrogen for 3 hr the reaction was placed under a hydrogen atmosphere overnight and was then sparged with hydrogen for a further 4 h. HPLC analysis indicated the presence of 98.5% product and 0.55% of a reaction intermediate (identity not confirmed, assumed to be the nitroso or hydroxylamine intermediate).

The reaction mixture was cooled to 48° C. and was passed through a Celite pad (24 g). The Celite pad was washed with DMF (2×160 mL) and as these washes contained catalyst they were passed through an inline filter. The combined filtrates were concentrated in vacuo to remove most of the 2-MeTHF providing a DMF/product solution. This mixture was added over 5 min to water (1.6 L) that was cooled with an ice/water bath (an exotherm was observed from 9.9-17.6° C.), providing a white suspension which was stirred at 18-25° C. for 1 hr. The solids were collected by filtration and the filter cake was washed with water (3×160 mL) and then dried in an oven at 50° C. to give the product as a white solid (75.5 g, HPLC purity 98.2%, 0.34% H$_2$O by KF, 6.56% DMF by $^1$H NMR).

The solid so obtained was slurried in DCM (400 mL) at 18-25° C. for 65 min, collected by filtration and the filter cake washed with DCM (2×160 mL). This material was then oven dried at 50° C. to give the title compound as a white solid (72.0 g, 65.9 g active product, 88% yield, HPLC purity 98.75%; containing 8.25%, DCM and 0.19% DMF by NMR); R$^t$ 11.01 min; m/z 472.4 (M+H)$^+$ (ES$^+$).

6-(4-(2-Chloro-5-methylnicotinamido)benzoyl)-N-(2-fluoro-6-methylphenyl)-5,6-dihydro-4H-benzo[b]thieno[2,3-d]azepine-2-carboxamide; Intermediate (IIIa)

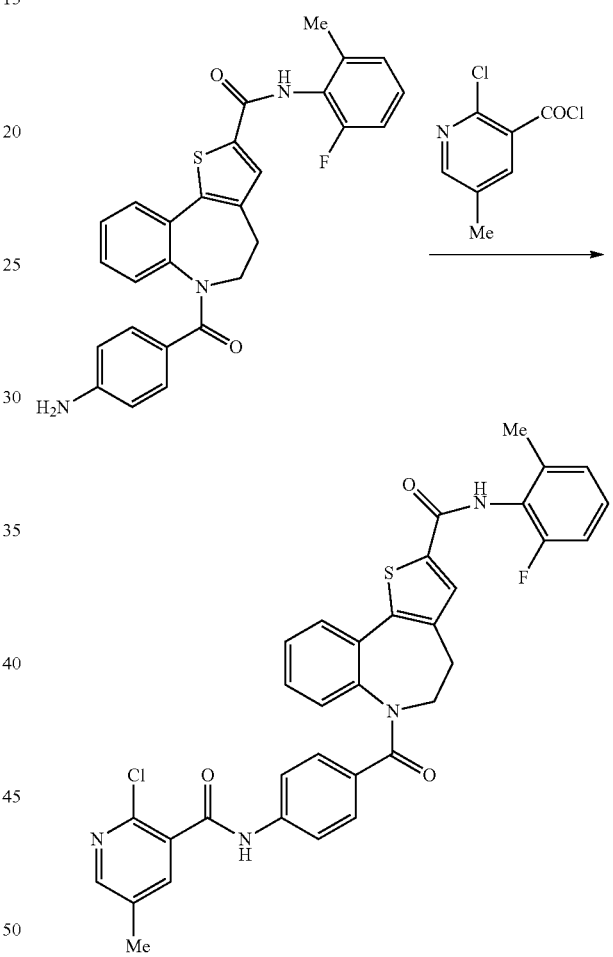

Oxalyl chloride (133 mL, 1.58 mol) was added to a suspension of 2-chloro-5-methyl nicotinic acid (225.4 g, 1.313 mol) in DCM (2254 mL) at 18-25° C. followed by DMF (0.8 mL, 0.010 mol) (results in mild exotherm and gas evolution) and the reaction stirred at 20-25° C. for 1 hr. HPLC analysis of an aliquot (quenched into methanol) indicated <1% of 2-chloro-5-methylnicotinic acid was remaining. The solvent was removed in vacuo and the oily residue was azeotroped with DCM (500 mL) to remove residual oxalyl chloride.

The resulting oil was taken up into DCM (413 mL) and was added dropwise over 10 min to a suspension of 6-(4-aminobenzoyl)-N-(2-fluoro-6-methylphenyl)-5,6-dihydro-4H-benzo[b] thieno[2,3-d]azepine-2-carboxamide (412.9 g, 0.876 mol) in a mixture of pyridine (283 mL, 3.502 mol) and DCM (28920 mL) whilst maintaining the internal temp <40° C. (maximum temp reached 38° C.). The reaction was stirred at 18-25° C. for 1 hr after which time HPLC (sample quenched into methanol) indicated the reaction was complete (<1% of aniline s/m remaining).

Heptane (3300 mL) was added to the mixture at 18-25° C. and the resulting suspension was stirred for 15 min and the solids then collected by filtration. The filter cake was washed with heptane (2×1650 mL) and the crude solid so obtained was slurried in water (4130 mL) at 90-95° C. for 30 min and then cooled to 18-25° C. The solids were collected by filtration, washed with water (2×826 mL) and dried in a vacuum oven at 50° C. to give the title compound as a white solid (504.2 g, 92% active yield, HPLC purity [230 nm] 98.24%; containing 0.3% pyridine HCl by $^1$H NMR and 0.4%.H$_2$O by KF); R$^t$ 12.19 min; m/z 625.6 (M+H)$^+$ (ES$^+$).

N-(2-Fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide: Compound (I)

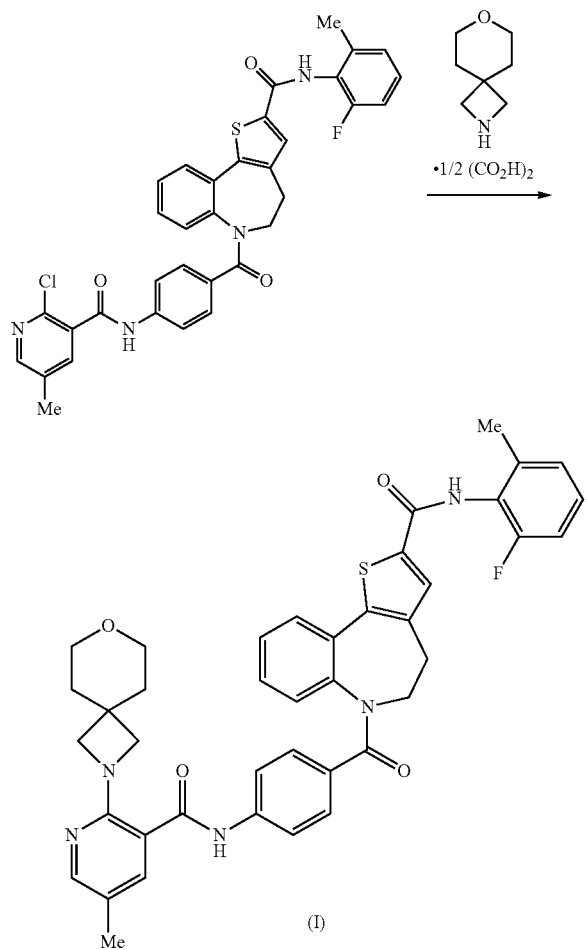

A suspension of 6-(4-(2-chloro-5-methylnicotinamido)benzoyl)-N-(2-fluoro-6-methylphenyl)-5,6-dihydro-4H-benzo[b]thieno[2,3-d]azepine-2-carboxamide (563.9 g, 0.902 mol), 7-oxa-2-azaspiro[3.5]nonane hemi oxalate (233.0 g, 1.353 mol) and potassium carbonate (374.0 g, 2.706 mol) in NMP (2820 mL) was stirred at 105-115° C. for 18 hr (HPLC analysis indicated the formation of 97.7% of the desired product and 0.02% of chloro-nicotinamide remaining).

The reaction was cooled to 18-25° C. and was added to water (8459 mL) with stirring at <45° C. (mildly exothermic quench). After stirring at 18-25° C. for 30 min, the resulting solid was collected by filtration, washed with water (2×1128 mL) and pulled dry. The crude product thus obtained was re-slurried in water (5640 mL) at 90-95° C. for 30 min, then cooled to 18-25° C., collected by filtration, washed with water (2×1260 mL) and dried in a vacuum oven at 50° C. to give a white solid (632.0 g).

The $^1$H NMR spectrum indicated 1.7% NMP to be present and the solid was re-slurried in water (5640 mL) at 90-95° C. for 30 min, cooled to 18-25° C., filtered, washed with water (2×1260 mL) and pulled dry. Further drying in a vacuum oven at 50° C. furnished the title compound, as a white solid (614.0 g, 95%, containing 0.75% NMP by $^1$H NMR and 1.7% H$_2$O by KF.) R$^t$ 9.48 min; m/z 716.8 (M+H)$^+$ (ES$^+$); $^1$H NMR δ: 1.60 (4H, br t), 2.16 (3H, s), 2.25 (3H, s), 3.14-3.30 (assume 3H, broad m, partly obscured by solvent), 3.44 (4H, br t), 3.59 (4H, s), 4.93 (1H, br d), 6.86 (1H, br d), 7.01 (2H, br d), 7.09-7.15 (3H, over-lapping m), 7.24-7.30 (2H, over-lapping m), 7.48 (1H, d), 7.51 (2H, br d), 7.82 (1H, d), 7.95 (1H, s), 8.02 (1H, d), 10.04 (1H, s), 10.39 (1H, s).

Biological Testing: Experimental Methods

Assessment of RSV Induced CPE in HEp2 Cells

HEp2 cells were seeded (10$^3$/well/50 μL) in 384-well plates (Catalogue number 353962, BD Falcon, Oxford, UK) in 5% serum free-DMEM containing 2 mM L-glutamine and 1 mM sodium pyruvate one day before infection. RSV A2 strain (#0709161v, NCPV, Public Health England, Wiltshire) or RSV B Washington strain (VR-1580, ATCC, Manassas, Va. 20108) virus solutions were prepared in serum free-DMEM with 2 mM L-glutamine and 1 mM sodium pyruvate, and then added (50 μL/well) to achieve a final virus concentration of 1 MOI. Simultaneously Compound (I) (0.5 μL DMSO solution) was added to 100 μL of HEp2 cell culture with virus solution to provide a final DMSO solution of 0.5%. Plates were incubated (37° C./5% CO$_2$) for 5 days for studies using RSV A2 strain or 6 days for those using RSV B strain, and then resazurin sodium salt (5 μL of 0.03% solution; Sigma-Aldrich, Dorset, UK) was added to each well and the plate incubated for a further 6 hr (37° C./5% CO$_2$). The fluorescence of each well [545 nm (excitation)/590 nm (emission)] was determined using a multi-scanner (Clariostar: BMG, Buckinghamshire, UK). The percentage inhibition for each well was calculated and the IC$_{50}$, IC$_{75}$ and IC$_{90}$ values were calculated from the concentration-response curve generated for Compound (I).

Assessment of RSV F Protein Expression in BEAS2B Bronchial Epithelial Cells

An early event which follows the infection of epithelial cells by RSV is the expression of RSV F-protein on the cells' surface. BEAS2B cells (SV40-immortalised human bronchial epithelial cell line) were grown in 96 well plates. Once more than 70% confluent, cells were infected with RSV A2 (#0709161v, NCPV, Public Health England, Wiltshire) at an MOI of 0.01 in clear RPMI-1640 medium (Life technologies, Paisley, UK) with 2% FBS (Life technologies, Paisley, UK), and incubated for 3 days (37° C./5% CO$_2$).

Supernatant was aspirated and the cells were fixed with 4% formaldehyde (100 μL in PBS solution) for 20 min, washed 3 times with washing buffer (200 μL; PBS containing 0.05% Tween-20) and incubated with blocking solution (100 µL; 5% Marvel milk in PBS) for 1 hr. Cells were then washed with washing buffer (200 µL) and incubated for 1 hr at 37° C. with anti-RSV (2F7; mouse monoclonal, lot 160290, Cat. No. ab43812, Abcam plc, Cambridge, UK) F-fusion protein antibody (50 µL; prepared at a 1:1000 dilution in 5% milk/PBS-tween). After washing, cells were incubated with an HRP-conjugated anti-mouse IgG antibody (50 µL prepared at a 1:2000 dilution in 5% milk in PBS; lot 00095437, Cat. No. P0447, Dako UK Ltd, Cambridgeshire, UK) for 1 hr. Cells were washed twice with washing buffer and once with PBS. TMB substrate (100 µL; substrate reagent pack lot 320436, Cat. No. DY999, R&D Systems, Inc. Abingdon, UK) was then added and the reaction was stopped by the addition of aq sulfuric acid (50 µL; 2N). The resultant signal was determined colourimetrically (OD: 450 nm with a reference wavelength of 655 nm) in a microplate reader (Multiskan FC®, ThermoFisher Scientific). Cells were then washed and 1% crystal violet solution (50 µL; lot SLB4576, Cat. No. HT90132-1L, Sigma-Aldrich) was applied for 30 min. After washing with PBS (200 µL) three times, 1% SDS (100 µL) was added to each well, and plates were shaken lightly for 1 hr prior to reading the absorbance at 595 nm. The measured $OD_{450-655}$ readings were corrected for cell number by dividing the $OD_{450-655}$ by the $OD_{595}$ readings. The percentage inhibition for each well was calculated and the $IC_{50}$ value derived from the concentration-response curve generated for Compound (I).

Cell Viability: Resazurin Assay

HEp2 cells were seeded in 384-well plates ($10^3$/well/50 µL; BD Falcon Ref 353962) in FBS DMEM (5%, containing 2 mM L-glutamine and 1 mM sodium pyruvate) one day before experimentation. Serum-free DMEM (50 µL) was added to test wells while for control wells the media was removed and sterile water (100 µL) was added. Compound (I) (0.5 µL DMSO solution) was added to give a final DMSO concentration of 0.5%. Hep2 cells were incubated with each test compound for 5 days (37° C./5% $CO_2$ in 5% FBS) and then resazurin stock solution (5 µL; 0.03%) was added to each well and the plate incubated for a further 6 hr (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment.

Any apparent increase in cell viability associated with test compound treatment relative to vehicle is consequently tabulated as a negative percentage. Where appropriate, a $CC_{50}$ value was calculated from the concentration-response curve generated for Compound (I).

Assessment of Virus Titre in Air-Liquid Interface (ALI) Cultured Bronchial Epithelial Cells ALI cultured human bronchial epithelial cells were sourced from Epithelix Sàrl (Geneva, Switzerland) and maintained by changing the basal media every 3-4 days, whilst the apical surface was washed once weekly with PBS. On day 0, the apical surface of each well was washed once with sterile PBS (300 µL) and the inserts were transferred to new 24-well plates containing fresh MucilAir culture medium (780 µL; EP04MM). RSV A2 (50 µL; diluted in MucilAir culture medium to give a final MOI of 0.01) was added to cells for 1 hr (37° C./5% $CO_2$). For the purposes of standardizing MOI calculations, each MucilAir insert was estimated to contain $2\times10^5$ apical facing cells per well. Virus inoculum was removed with a pipette and inserts were washed twice with sterile PBS (300 µL).

Sampling was conducted by adding sterile PBS (300 µL) to the apical surface of each well for 5 min. The apical sample was then removed and transferred to tubes containing 50% sucrose dissolved in PBS (100 µL) before being stored at −80° C. This harvesting procedure was repeated daily beginning on day 0 and concluding on day 7.

ALI cultures were dosed apically with Compound (I) on days 0-7 for "early intervention" protocols, or days 3-7 for "late intervention" protocols. Compound (I) (50 µL in 0.5% DMSO/PBS) was added to the apical surface and incubated (37° C./5% $CO_2$) for 1 hr before being removed. Vehicle treatments (0.5% DMSO/PBS) were performed on the corresponding apical surfaces to ensure each well received the same number of manipulations. On Day 5, the basal media was removed from each well and replenished with fresh MucilAir culture media as a necessary maintenance step for ALI culture cells.

Virus titre was quantified by plaque assay. HEp2 cells were grown in 24-well plates (Corning) for 48 hr prior to infection in DMEM containing 10% FBS until they attained 100% confluency. Collected samples were thawed at RT and ten-fold serial dilutions were prepared in serum-free DMEM. The growth medium from HEp2 cells was aspirated and replaced with 300 µL of serially diluted virus collections and left to infect at 37° C./5% $CO_2$ for 4 hr. The infectious media was aspirated and replaced with Plaque Assay Overlay (500 µL; 1% methylcellulose in MEM, 2% FBS, 1% Pen Strep, 0.5 µg/mL amphotericin B), and left for 7 days at 37° C./5% $CO_2$. Cells were fixed with ice-cold methanol for 10 min and blocked with 5% powdered milk (Marvel) in 0.05% PBS-tween ('blocking buffer') for 1 hr at RT. Anti-RSV F-protein antibody (2F7; Abcam: ab43812) was diluted to a 1:100 concentration in blocking buffer and added to cells for 1 hr at RT with shaking. Cells were washed using PBS and incubated with the secondary antibody (HRP conjugated goat anti-mouse secondary antibody (Dako P044701-2) diluted in 1:400 with blocking buffer) for 1 hr at RT with shaking. The secondary antibody solution was removed and cells were washed with PBS before the metal-enhanced development substrate DAB was prepared in ultra-pure water (according to manufacturer's instructions). Each well received 300 µL of development substrate (sigmaFAST D0426) until plaques were visible. Plaques were counted by eye and confirmed using light microscopy, allowing the calculation of plaque forming units per mL.

RSV Infection in Mice

Non-fasted mice (male BALB/C, 20-30 g) were infected intranasally with RSV A2 or virus diluent (DMEM, 2% FBS, 12.5% sucrose) under isoflurane (5% in $O_2$) anaesthesia. The A2 strain of RSV (50 uL of $1.3\times10^6$ PFU/mL: final $0.65\times10^5$ PFU/mouse) was instilled into each nostril in a drop wise fashion alternating between the two until a volume of 50 µL was delivered. Following infection each animal was weighed on a daily basis to monitor changes. Compound (I) was dissolved in 100% DMSO (at 20 mg/mL and/or 2 mg/mL), then diluted at 1:10 in isotonic saline to achieve 10% DMSO in all treatments. Formulations were then sonicated to produce a suspension. The suspension was administered intratracheally (20 µL) with a FMJ-250 Penn-Century device or intranasally (40 µL) with a pipette on 1 day and 1 hr before infection (day 0), and then on days 1, 2 and 3 post infection. Four days after RSV challenge, the animals were euthanised (by intraperitoneal injection of a pentobarbitone overdose), the trachea cannulated and BALF extracted for total and differential cell counts. Following BALF collection, the right lung was removed from each animal and homogenised in ice-cold Dulbecco's modified Eagles medium (using 10 times the lung weight of DMEM containing 1% BSA and 25% sucrose) for 2×20 second bursts. The homogenate was then transferred into a sterile tube and spun at 4° C. (2000 rpm; for 5 min). The clarified homogenate was transferred to a chilled cryovial, snap frozen and stored at −80° C. The supernatants from lung homogenates were used for the plaque assay.

HEp2 cells were grown in 24-well plates (Corning) for 48 hr prior to infection in DMEM containing 10% FBS until they attained 100% confluency. Lung homogenate was thawed at RT and ten-fold serial dilutions were prepared in serum-free DMEM. The growth medium from HEp2 cells was aspirated and replaced with 300 μL of serially diluted lung homogenate and left to infect (4 h; 37° C./5% $CO_2$). The infectious media were aspirated and replaced with Plaque Assay Overlay (500 μL; 1% methylcellulose in MEM, 2% FBS, 1% Pen Strep, 0.5 μg/mL amphotericin B), and left for 7 days (37° C./5% $CO_2$). Cells were fixed with ice-cold methanol for 10 min and blocked with 5% powdered milk (Marvel) in 0.05% PBS-tween (blocking buffer) for one hr at RT.

Anti-RSV F-protein antibody [2F7] (Abcam: ab43812) was diluted to a 1:100 concentration in blocking buffer and added to cells for 1 hr at RT with shaking. Cells were washed using PBS and then incubated with the secondary antibody (HRP conjugated goat anti-mouse secondary antibody (Dako P044701-2) diluted in 1:400 with blocking buffer) for 1 hr at RT with shaking. The secondary antibody solution was removed and cells were washed with PBS before the metal-enhanced development substrate DAB was prepared in ultra-pure water (according to manufacturer's instructions). Each well received 300 μL of development substrate (sigmaFAST D0426) until plaques were visible. Plaques were counted by eye and confirmed using light microscopy, allowing the calculation of plaque forming units per mL of lung homogenate supernatant.

RSV Infection in Cotton Rats

Male *Sigmodon hispidus* cotton rats between 6 and 8 weeks of age were infected with hRSV/A/Long (ATCC, Manassas, Va.; $10^5$ pfu) in a volume of 0.1 mL of sucrose stabilizing media. Compound (I) was dissolved in 100% DMSO (at 3.3, 10, 33 and 100 mg/mL), then diluted at 1:10 in isotonic saline to achieve 10% DMSO in all treatments. Formulations were then sonicated to produce suspensions. The resulting suspensions were administered intranasally (50 μL) by pipette 4 hr before infection (on day 0), and then on days 1, 2 and 3 post infection. Four days after RSV challenge, the animals were euthanised and the lungs were removed. The left lobe was used for viral titration via plaque assay and the lingular lobe for RSV/A/Long NS-1 qRT-PCR and cytokine qRT-PCR.

The supernatant of lung homogenates were diluted 1:10 and 1:100 in Eagle (E)-MEM. Confluent HEp-2 monolayers in 24-well plates were infected in duplicate (50 μL of sample per well) starting with undiluted (neat) samples followed by diluted homogenates. After incubation for 1 hr (37° C./5% $CO_2$) wells were overlaid with 0.75% methylcellulose medium and plates replaced in the 37° C. incubator. After incubation (for 4 days), the overlay was removed, the cells fixed with 0.1% crystal violet stain (for 1 hr) and then rinsed and air-dried. Plaques were counted and viral titers were expressed as plaque forming units per gram ($pfu \cdot g^{-1}$) of tissue.

Total RNA was also extracted from homogenized lung tissue (RNeasy purification kit; Qiagen) and a sample (1 μg) was used to prepare cDNA using QuantiTect Reverse Transcription Kit (Qiagen). For real-time PCR reactions (RSV NS-1 and RANTES genes) the QuantiFast SYBR® Green PCR Kit (Qiagen) was used in a final volume of 25 μL, with final primer concentrations of 0.5 μM. Amplifications were performed on a Bio-Rad iCycler for 1 cycle of 95° C. for 3 min, followed by 40 cycles of 95° C. for 10 sec, 60° C. for 10 sec, and 72° C. for 15 sec. Baseline cycles and cycle threshold (Ct) were calculated by the iQ5 software in the PCR Base Line Subtracted Curve Fit mode. The standard curves were developed using serially diluted cDNA sample most enriched in the transcript of interest (e.g., lungs from day 4 post-primary RSV infection). The Ct values were plotted against login cDNA dilution factor. These curves were used to convert the Ct values obtained for different samples to relative expression units which were then normalized to the level of β-actin mRNA ("housekeeping gene") expressed in the corresponding sample. The mRNA levels were expressed as the geometric mean±SEM for all animals in a group.

In Vitro Screening Results

The profile of Compound (I), as disclosed herein, is summarised below (Table A) and demonstrates potent inhibitory activities against both RSV A2-induced CPE and RSV B-induced CPE in HEp2 cells. Furthermore, the compound of the invention exhibits potent inhibition of RSV A2 F-protein expression in BEAS2B bronchial epithelial cells. No effect on cell viability, resulting from incubation with Compound (I), was detected.

TABLE A

The effects of treatment with Compound (I) on RSV A2- and RSV B-induced CPE in HEp2 cells, on RSV A2 F-protein expression in BEAS2B bronchial epithelial cells and on cell viability.

| | $IC_{50}/CC_{50}$ Values (nM) or Inhibition (%) at indicated concentration | | | | | |
|---|---|---|---|---|---|---|
| | RSV A2 CPE | | RSV B CPE | | RSV A2 F-protein | Cell Viability |
| Treatment | $IC_{50}$ (nM) | % Inhibition[1] | $IC_{50}$ (nM) | % Inhibition[2] | $IC_{50}$ (nM) | $CC_{50}$ (nM) |
| Compound (I) | 0.017 | 100 | 10.2 | 72 | 0.17 | >14000 |

Table Footnotes:
[1]Inhibition (%) at 0.1 μg/mL;
[2]Inhibition (%) at 1 μg/mL;

Anti-viral effects were also evaluated using air-liquid cultured human primary bronchial epithelial cells. The cells undergo extensive mucociliary differentiation, resulting in cultures with morphological characteristics similar to those observed in the normal human respiratory epithelium. As a result, this cell model closely mimics RSV infections in human airways.

Figure 2:
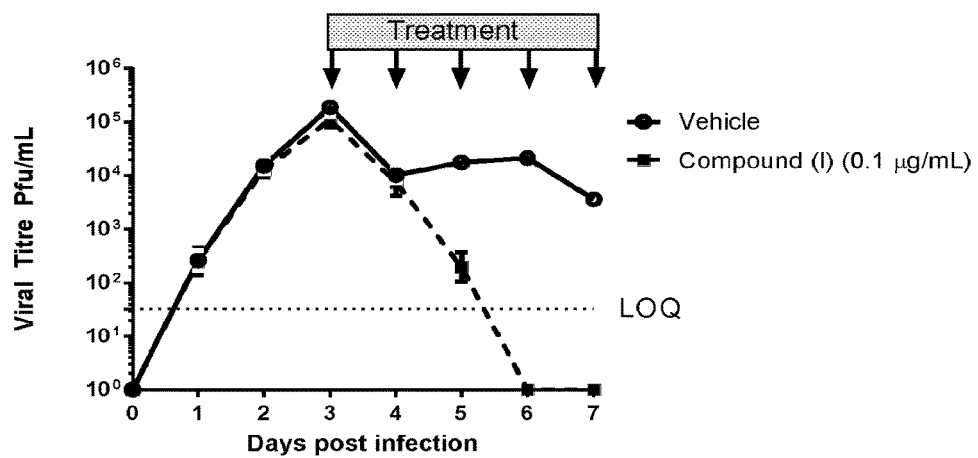
FIG. 2 shows the effect of Compound (I) on virus titre in RSV A2 infected air-liquid interface (ALI) cultured epithelial cells following late intervention with test compound

The RSV titre increased from day 1, peaked at day 3 and then gradually and moderately reduced up to day 7. Treatment with Compound (I) to an apical well daily from day 0 to day 7 (early intervention, see Table B, FIG. 1) induced concentration dependent inhibition, and showed complete inhibition at 0.1 μg/mL over 7 days. Treatment with Compound (I) also produced a dramatic reduction of virus titre on days 6 and 7 post infection when it was administered from day 3 after the virus peak (Late intervention, see Table C, FIG. 2).

strains. Compound (I) was therefore tested in the above mentioned in vivo systems.

Figure 3:
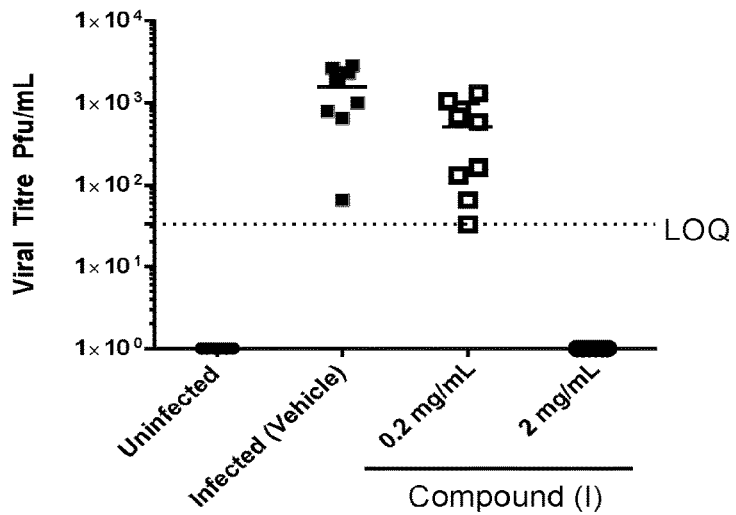
FIG. 3 shows the effect of Compound (I) on virus titre in the lungs of RSV A2 infected mice

In RSV A2 infected mice, virus titre peaked on day 4 following inoculation. Compound (I) was administered 1 day and 1 hr before inoculation (day 0) and then 2 and 3 days after virus infection either intranasally (Table D, FIG. 3) or intratracheally (Table E) and in both cases demonstrated potent dose-dependent inhibition of viral titre in lung homogenates.

TABLE B

The effects of early intervention (days 0-7) with Compound (I) on RSV A2 viral titre in apical wash from RSV A2 infected, air-liquid interface cultured, bronchial epithelial cells.

| Treatment | Drug Conc. mg/mL | Virus titre in apical wash on days indicated expressed as the geometric mean (log PFU/mL) ± SD[1,2] | | | | | | | |
|---|---|---|---|---|---|---|---|---|---|
| | | 0 | 1 | 2 | 3 | 4 | 5 | 6 | 7 |
| Vehicle plus virus | none | 0.0 ± 0.0 | 0.94 ± 1.3 | 4.0 ± 0.18 | 4.5 ± 0.15 | 3.7 ± 0.22 | 4.1 ± 0.22 | 4.1 ± 0.22 | 3.5 ± 0.31 |
| Compound (I) plus virus | 0.004 | 0.0 ± 0.0 | 0.61 ± 0.86 | 3.1 ± 0.22 | 3.9 ± 0.18 | 4.1 ± 0.16 | 4.2 ± 0.12 | 3.2 ± 0.26 | 2.8 ± 0.43 |
| | 0.02 | 0.0 ± 0.0 | 0.0 ± 0.0 | 0.0 ± 0.0 | 0.0 ± 0.0 | 1.4 ± 1.1 | 1.9 ± 1.4 | 0.0 ± 0.0 | 0.0 ± 0.0 |
| | 0.1 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |

[1]Allocated 1 PFU/mL if any plaque was detected in the assay with ×10 diluted apical wash;
[2]The n values were 3 for all experiments.

TABLE C

The effects of late intervention (days 3-7) with Compound (I) on RSV A2 viral titre in apical wash from RSV A2 infected air-liquid interface cultured bronchial epithelial cells.

| Treatment | Drug Conc. mg/mL | Virus titre in apical wash on days indicated expressed as the geometric mean (log PFU/mL) ± SD[1,2] | | | | | | | |
|---|---|---|---|---|---|---|---|---|---|
| | | 0 | 1 | 2 | 3 | 4 | 5 | 6 | 7 |
| Vehicle plus virus | none | 0.0 ± 0.0 | 2.4 ± 0.26 | 4.2 ± 0.12 | 5.2 ± 0.18 | 4.0 ± 0.14 | 4.2 ± 0.17 | 4.0 ± 0.50 | 3.5 ± 0.22 |
| Compound (I) plus virus | 0.02 | 0.0 ± 0.0 | 1.6 ± 1.1 | 3.9 ± 0.15 | 5.2 ± 0.04 | 3.8 ± 0.50 | 3.6 ± 0.13 | 0.0 ± 0.0 | 1.3 ± 0.94 |
| | 0.1 | 0.0 ± 0.0 | 2.3 ± 0.35 | 4.1 ± 0.14 | 5.0 ± 0.14 | 3.8 ± 0.31 | 1.7 ± 1.2 | 0.0 ± 0.0 | 0.0 ± 0.0 |

[1]Allocated 1 PFU/mL if any plaque was detected in the assay with ×10 diluted apical wash;
[2]The n values were 3 for all experiments.

In Vivo Testing

Human RSV is able to infect and replicate in a number of animal species used for pre-clinical screening, thereby enabling the performance and profiles of novel anti-infective agents to be assessed and compared in vivo (Bem, et al., 2011). Although primate species can also be infected and studied, most work of this nature is conducted in mice or cotton rats. Both standard, inbred mouse strains and cotton rats are characterised as "semi-permissive" for the replication of human RSV, although significantly greater viral replication is seen in cotton rats compared to inbred mouse

TABLE D

The effects of intranasal treatment with Compound (I) on RSV A2 viral titre in lung from RSV A2 infected mice.

| Treatment | Drug Conc (mg/mL) | Virus titre (log PFU/lung)[1] | | |
|---|---|---|---|---|
| | | Geometric mean | Median | Interquartile range |
| Vehicle plus virus | none | 3.0 | 3.2 | 2.8-3.4 |

TABLE D-continued

The effects of intranasal treatment with
Compound (I) on RSV A2 viral titre in
lung from RSV A2 infected mice.

| Treatment | Drug Conc (mg/mL) | Virus titre (log PFU/lung)[1] | | |
|---|---|---|---|---|
| | | Geometric mean | Median | Interquartile range |
| Compound (I) plus virus | 0.2 | 2.4 | 2.5 | 1.9-3.0 |
| | 2 | <1.5[2] | <1.5[2] | |

[1]n values were 8 for all experiments;
[2]Lower limit of quantitation (LOQ).

TABLE E

The effects of intratracheal treatment with
Compound (I) on RSV A2 viral titre in
lung from RSV A2 infected mice.

| Treatment | Drug Conc (mg/mL) | Virus titre (log PFU/lung)[1] | | |
|---|---|---|---|---|
| | | Geometric mean | Median | Interquartile range |
| Vehicle plus virus | none | 3.1 | 3.1 | 2.7-3.4 |
| Compound (I) plus virus | 0.2 | <1.5[2] | <1.5[2] | |

[1]n values were 8 for all experiments;
[2]Lower limit of quantitation (LOQ).

Figure 4:
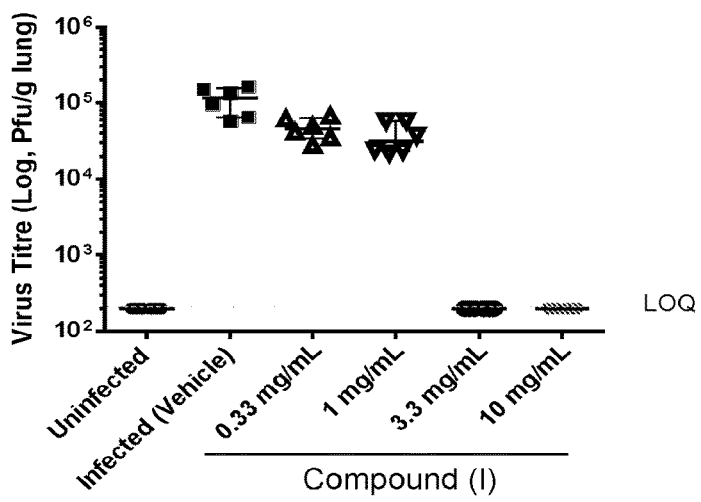
FIG. 4 shows the effect of Compound (I) on virus titre in the lungs of RSV A2 infected cotton rats

The potent dose-dependent inhibition of virus titre by Compound (I) was also seen in lung homogenates from RSV/S/Long infected cotton rats on day 4 (Table F, FIG. 4). In addition, the drug substance displayed a dose-dependent inhibition of RSV NS-1 gene transcripts (Table G) and of RANTES transcripts in lung (Table H).

TABLE F

The effects of intranasal treatment with
Compound (I) on RSV A2 viral titre in lung
from RSV A2 infected cotton rats.

| Treatment | Drug Conc (mg/mL) | Virus titre (log PFU/lung)[1] | | |
|---|---|---|---|---|
| | | Geometric mean | Median | Interquartile range |
| Vehicle | none | <2.3[2] | <2.3[2] | — |
| Vehicle plus virus | none | 5.0 | 5.1 | 4.8-5.2 |
| Compound (I) plus virus | 0.33 | 4.7 | 4.7 | 4.5-4.8 |
| | 1.0 | 4.5 | 4.5 | 4.4-4.8 |
| | 3.3 | <2.3[2] | <2.3[2] | — |
| | 10 | <2.3[2] | <2.3[2] | — |

[1]n values were 6 for all experiments;
[2]Lower limit of quantitation (LOQ).

TABLE G

The effects of intranasal treatment
with Compound (I) on RSV A2 NS-1 gene
expression in lung from RSV A2 infected cotton rats.

| Treatment | Drug Conc (mg/mL) | RSV NS1 gene transcript (/β-actin)[1] | | |
|---|---|---|---|---|
| | | Median | Interquartile range | % inhibition |
| Vehicle | none | 0 | 0-0 | — |
| Vehicle plus virus | none | 4.4 | 2.4-6.4 | — |
| Compound (I) plus virus | 0.33 | 2.0 | 1.7-2.5 | 55% |
| | 1.0 | 1.6 | 1.2-3.0 | 64% |
| | 3.3 | 1.0 | 0.33-2.4 | 77% |
| | 10 | 1.0 | 0.36-2.2 | 77% |

[1]n values were 6 for all experiments.

TABLE H

The Effects of intranasal treatment
with Compound (I) on RANTES gene
expression in lung from RSV A2 infected cotton rats.

| Treatment | Drug Conc (mg/mL) | RANTES gene transcript (/β-actin)[1] | | |
|---|---|---|---|---|
| | | Median | Interquartile range | % inhibition |
| Vehicle | none | 0.088 | 0.046-0.090 | — |
| Vehicle plus virus | none | 0.29 | 0.21-0.40 | — |
| Compound (I) plus virus | 0.33 | 0.21 | 0.16-0.33 | 28 |
| | 1.0 | 0.16 | 0.15-0.25 | 45 |
| | 3.3 | 0.11 | 0.075-0.15 | 62 |
| | 10 | 0.13 | 0.13-0.17 | 55 |

[1]n values were 6 for all experiments.

SUMMARY

The in vitro antiviral activity of the compound of the invention has been demonstrated by its cytoprotective effect on HEp2 cells, infected with RSV. In this assay system the inhibition of virus replication was detected and quantified from the resulting inhibition of virus-mediated CPE. It is particularly noteworthy that Compound (I) is a potent inhibitor of the CPE induced by both the RSV A strain the RSV B strain studied. The potent antiviral activity of Compound (I) was further evidenced by its inhibition of RSV A2 F-protein expression in BEAS2B cells.

The compound of the invention demonstrates low mammalian cell toxicity as measured by its lack of any significant effect in the cell viability assay. Furthermore, in an in vitro model of human lung epithelium, comprising an air-liquid interface culture of bronchial epithelial cells, the compound of the invention completely inhibited virus titre when administered by either early or late stage intervention. The latter observation is particularly significant for the treatment of established disease.

The in vivo antiviral activity of the compound of the invention has been demonstrated in mice and cotton rats infected with RSV. In the assay systems the inhibition of virus replication was detected and quantified from the RSV titre in lung homogenates as measured in a plaque assay. In keeping with the data obtained from the studies conducted in ALI-cultured human bronchial cells, Compound (I) completely inhibited virus titre in the lungs of RSV A2 infected mice and cotton rats. The compound of the invention thus has the necessary attributes to be an effective medicine for the treatment and/or prevention of RSV infection and associated disease.

REFERENCES

Abman S. H., Ogle J. W., Butler-Simon N., Rumack C. M., and Accurso F. J. Role of respiratory syncytial virus in early hospitalizations for respiratory distress of young infants with cystic fibrosis. *J. Pediatr.,* 1988, 113, 826-30.

Bern R. A., Domachowske J. B. and Rosenberg, H. F. Animal models of human respiratory syncytial disease. *Am. J. Physiol.,* 2011. 301, L148-L156.

Hall C. B., Douglas R. G. Jr., Schnabel K. C. and Geiman J. M. Infectivity of respiratory syncytial virus by various routes of inoculation. *Infect. Immun.,* 1981, 33, 779-83.

Holt P. G. and Sly P. D. Interactions between RSV infection, asthma, and atopy: unravelling the complexities. *J. Exp. Med.,* 2002, 196, 1271-1275.

Johnson J. E., Gonzales R. A., Olson S. J., Wright P. F. and Graham, B. S. The histopathology of fatal untreated human respiratory syncytial virus infection. *Modern Pathology,* 2007, 20, 108-119.

Lee N., Lui G. C., Wong K. T., Li T. C., Tse E. C., Chan J. Y., Yu J., Wong S. S., Choi K. W., Wong R. Y., Ngai K. L., Hui D. S. and Chan P. K. High morbidity and mortality in adults hospitalized for respiratory syncytial virus infections. *Clin. Infect. Dis.,* 2013, 57, 1069-77.

Mohan A., Chandra S., Agarwal D., Guleria R., Broor S., Gaur B. and Pandey R. M. Prevalence of viral infection detected by PCR and RT-PCR in patients with acute exacerbation of COPD: A systematic review. *Respirology,* 2010, 15, 536-542.

Newcomb D. C. and Peebles R. S. Jr. Bugs and asthma: a different disease? *Proc. Am. Thorac. Soc.,* 2009, 1; 6, 266-71.

Olivier A., Gallup J., de Macedo M. M. M. A., Varga S. M. and Ackermann M. Human respiratory syncytial virus A2 strain replicates and induces innate immune responses by respiratory epithelia of neonatal lambs. *Int. J. Exp. Pathol.,* 2009, 90, 431-438.

Panayiotou C., Richter J., Koliou M., Kalogirou N., Georgiou E. and Christodoulou C. Epidemiology of respiratory syncytial virus in children in Cyprus during three consecutive winter seasons (2010-2013): age distribution, seasonality and association between prevalent genotypes and disease severity. *Epidemiol. Infect.,* 2014, Jan. 24, 1-6.

Walsh E. E., McConnochie K. M., Long C. E. and Hall C. B. Severity of respiratory syncytial virus infection is related to virus strain. *J. Infect. Dis.,* 1997, 175, 814-20.

Zhang Z-Y., Du L-N., Chen X., Zhao Y., Liu, E-M., Yang X-Q. and Zhao X-D Genetic variability of respiratory syncytial viruses (RSV) prevalent in Southwestern China from 2006 to 2009: emergence of subgroup B and A RSV as dominant strains. *J. Clin. Microbiol.,* 2010, 48, 1201-7.

Zhu Q., McAuliffe J. M., Patel N. K., Palmer-Hill F. J., Yang C. F., Liang B., Su L., Zhu W., Wachter L., Wilson S., MacGill R. S., Krishnan S., McCarthy M. P., Losonsky G. A. and Suzich J. A. Analysis of respiratory syncytial virus preclinical and clinical variants resistant to neutralization by monoclonal antibodies palivizumab and/or motavizumab. *J Infect. Dis.,* 2011, 203, 674-82.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A process for the preparation of a compound of formula (I):

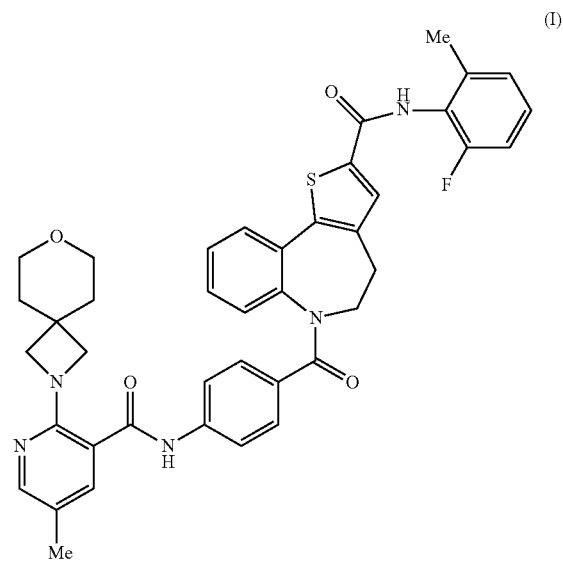 [SMILES: Cc1cnc(N2CC3(CCOCC3)C2)c(C(=O)Nc2ccc(C(=O)N3CCc4cc(C(=O)Nc5c(C)cccc5F)sc4-c4ccccc43)cc2)c1]

or a pharmaceutically acceptable salt thereof which comprises:

reacting a compound of formula (II)

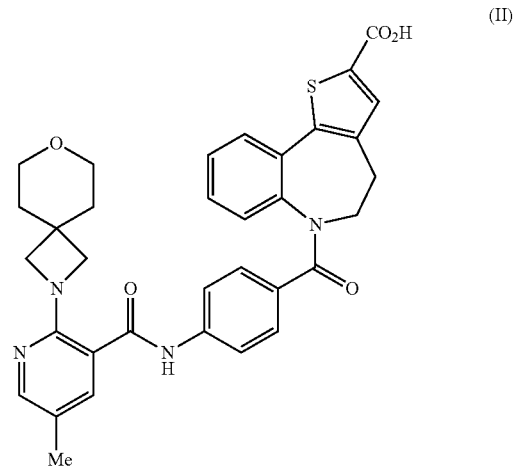 [SMILES: Cc1cnc(N2CC3(CCOCC3)C2)c(C(=O)Nc2ccc(C(=O)N3CCc4cc(C(=O)O)sc4-c4ccccc43)cc2)c1]

or a salt thereof;

with 2-fluoro-6-methylaniline; or reacting a compound of formula (III)

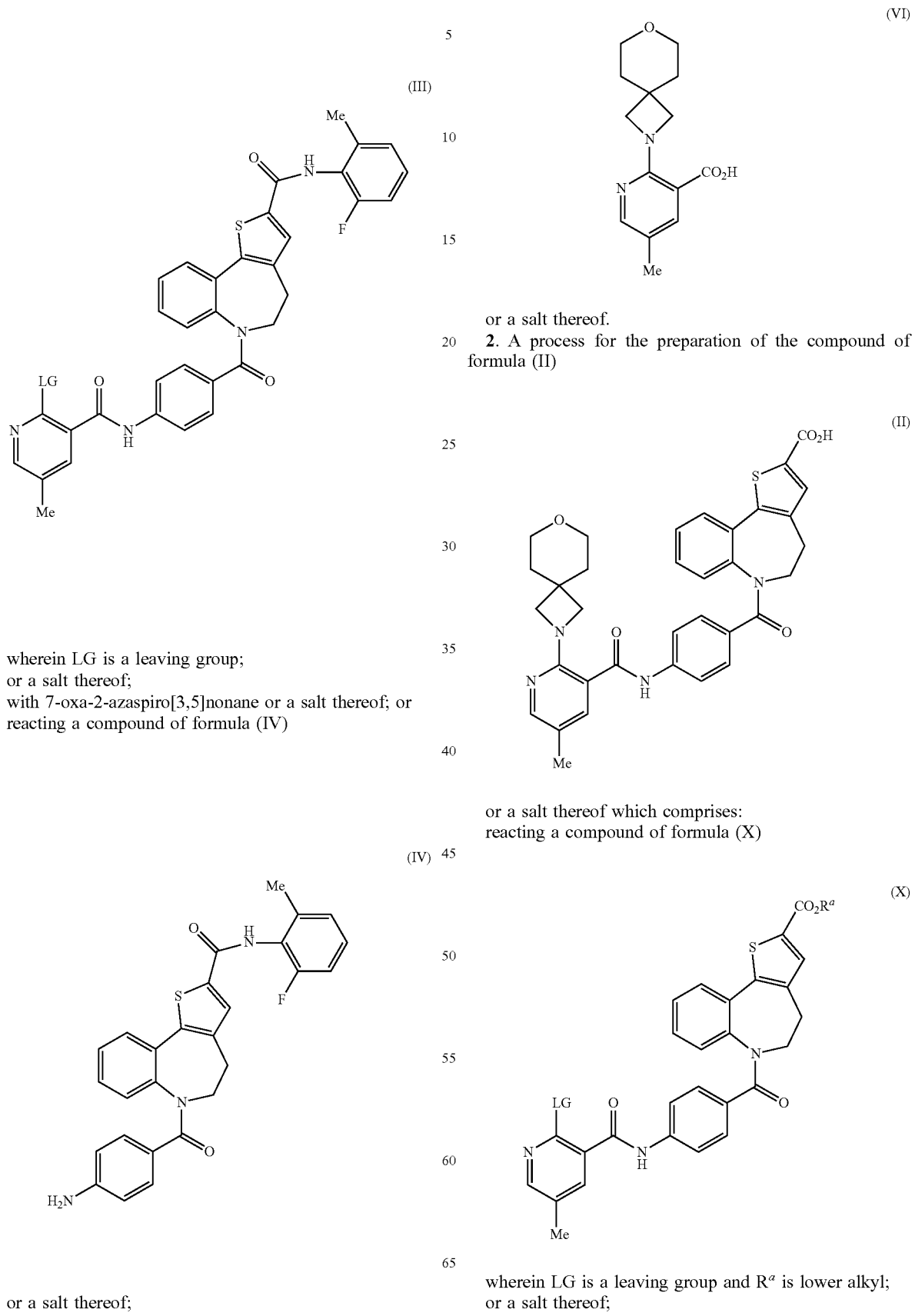

with the compound of formula (VI)

or a salt thereof.

2. A process for the preparation of the compound of formula (II)

or a salt thereof which comprises:
reacting a compound of formula (X)

wherein LG is a leaving group;
or a salt thereof;
with 7-oxa-2-azaspiro[3,5]nonane or a salt thereof; or
reacting a compound of formula (IV)

or a salt thereof;

wherein LG is a leaving group and $R^a$ is lower alkyl;
or a salt thereof;

with 7-oxa-2-azaspiro[3,5]nonane or a salt thereof, followed by hydrolysis of the carboxylate ester to the free acid; or reacting a compound of formula (IX)

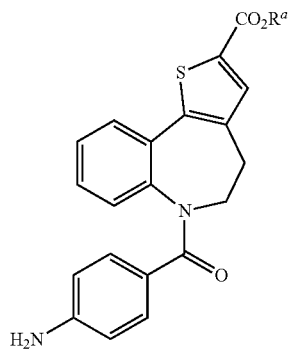
(IX)

wherein $R^a$ is lower alkyl;
or a salt thereof;

with a compound of formula (VI)

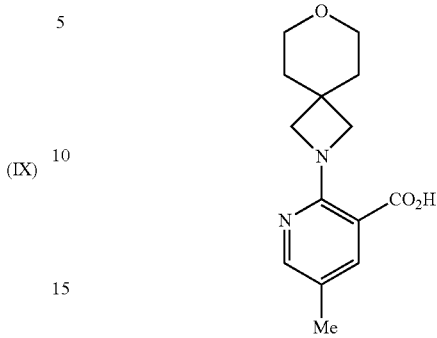
(VI)

or a salt thereof;
followed by hydrolysis of the carboxylate ester to the free acid.

3. The process according to claim 1 wherein the leaving group is a halogen atom.

4. The process according to claim 3 wherein the halogen atom is chlorine.

5. The process according to claim 2 wherein the leaving group is a halogen atom.

6. The process according to claim 5 wherein the halogen atom is chlorine.

7. The process according to claim 2 wherein the lower alkyl group is ethyl.

* * * * *

UNITED STATES PATENT AND TRADEMARK OFFICE
CERTIFICATE OF CORRECTION

PATENT NO. : 10,035,810 B2
APPLICATION NO. : 15/902077
DATED : July 31, 2018
INVENTOR(S) : Simon Fraser Hunt et al.

It is certified that error appears in the above-identified patent and that said Letters Patent is hereby corrected as shown below:

On the Title Page

Item (72) Inventors should read:
Inventors: Simon Fraser Hunt, Nottingham (GB); Stuart Thomas Onions, Nottingham (GB); Vladimir Sherbukhin, Nottingham (GB); Euan Alexander Fraser Fordyce, Nottingham (GB); Peter John Murray, London (GB); Daniel William Brookes, London (GB); Kazuhiro Ito, London (GB); Peter Strong, London (GB); Matthew Stephen Coates, London (GB)

Signed and Sealed this
Sixth Day of August, 2019

Andrei Iancu
*Director of the United States Patent and Trademark Office*